US006762176B1

(12) United States Patent
Chabrier de Lassauniere et al.

(10) Patent No.: US 6,762,176 B1
(45) Date of Patent: Jul. 13, 2004

(54) 2-AMINOPYRIDINE DERIVATIVES, THEIR USE AS MEDICINES AND PHARMACEUTICAL COMPOSITIONS CONTAINING THEM

(75) Inventors: Pierre-Etienne Chabrier de Lassauniere, Paris (FR); Serge Auvin, Mauchamps (FR); Jerry Harnett, Gif-sur-Yvette (FR); Dominique Pons, Paris (FR); Gérard Ulibarri, Fraze (FR); Dennis Bigg, Gir-sur-Yvette (FR)

(73) Assignee: Societe de Consells de Recherches et D'Applications Scientifiques (S.C.R.A.S.), Paris (FR)

( * ) Notice: Subject to any disclaimer, the term of this patent is extended or adjusted under 35 U.S.C. 154(b) by 0 days.

(21) Appl. No.: 09/743,043

(22) PCT Filed: Jul. 5, 1999

(86) PCT No.: PCT/FR99/01610

§ 371 (c)(1),
(2), (4) Date: Mar. 8, 2001

(87) PCT Pub. No.: WO00/02860

PCT Pub. Date: Jan. 20, 2000

(30) Foreign Application Priority Data

Jul. 8, 1998 (FR) .............................................. 98 08732
Apr. 2, 1999 (FR) .............................................. 99 04133

(51) Int. Cl.$^7$ ...................... A61K 31/33; A61K 31/44; C07D 213/73; C07D 213/00
(52) U.S. Cl. ...................... 514/183; 514/345; 514/352; 514/357; 546/290; 546/304; 546/329
(58) Field of Search ................................ 514/183, 343, 514/352, 357, 353; 546/290, 304, 329

(56) References Cited

U.S. PATENT DOCUMENTS

| 3,037,988 A | 6/1962 | Semb et al. ............. 260/245.5 |
| 4,180,574 A | 12/1979 | Stein .......................... 424/290 |

FOREIGN PATENT DOCUMENTS

| DE | 2830351 | 1/1980 |
| EP | 0790240 | 8/1997 |
| HU | 212230 | 7/1994 |
| JP | 62223173 | * 10/1987 |
| WO | 9618616 | * 6/1996 |
| WO | 9630350 | 10/1996 |
| WO | 9824766 | * 6/1998 |

OTHER PUBLICATIONS

Chabrier et al, "NOS:targets for thera. stratergies in ND", Cell Mol LifeSc.,55, 1029–35(1999).;PubMed:10442086.*
Nathan, FASEB,"NO as . . . mammalian cells";6, 3051–64(1992).*
Feldman,C & EN, "The surprising life of NO",Dec. 20, 27–38(1993).*
Le Corvoisier et al,"Role of NO",J.Soc.Biol. 194, 143–9(2000).;PubMed Abs.:11324316.*
Bogdan,"NO and the immune response",Nat Imm. 2/10, 907016(2001).;PubMed:11577346.*
Himbert et al, "Synthesis . . . butadienamides", 6001 Chemical Abstracts, Columbus, Ohio, US, vol. 125 (1996) 26–08, No. 9, p. 1136.
Curran et al, "Radical . . . Carbonyl Groups", 6001 Chemical Abstracts, Columbus, Ohio, US, vol. 115 (1991) 16–09, No. 11, p. 860.
Kutschy et al, "Selectivity . . . Group", 6001 Chemical Abstracts, Columbus, Ohio, US, vol. 108 (1988) 15–02, No. 7, p. 679.
Okamoto et al, "4–Pyridylureas . . . Relationship", Chem. Pharm. Bull., vol. 29 (1981), pp. 3748–3750.

* cited by examiner

*Primary Examiner*—Richard L. Raymond
*Assistant Examiner*—Sudhaker B. Patel
(74) *Attorney, Agent, or Firm*—Muserlian and Lucas and Mercanti, LLP

(57) ABSTRACT

The invention concerns novel 2-aminopyridine derivatives having an activity inhibiting NO-synthase enzymes producing nitrogen monoxide NO and/or trapping reactive forms of oxygen, the methods for preparing them, pharmaceutical compositions containing them and their therapeutic uses, particularly their use as NO-synthase inhibitors and for trapping reactive forms of oxygen whether selectively or not.

15 Claims, No Drawings

2-AMINOPYRIDINE DERIVATIVES, THEIR USE AS MEDICINES AND PHARMACEUTICAL COMPOSITIONS CONTAINING THEM

This application is a 371 of PCT/FR99/01610 filed Jul. 5, 1999.

A subject of the present invention is new derivatives of 2-aminopyridines which have an inhibitory activity on NO-synthase enzymes producing nitrogen monoxide NO and/or an activity which traps the reactive oxygen species (ROS). The invention relates to the derivatives corresponding to general formula (I) defined below, their preparation methods, the pharmaceutical preparations containing them and their use for therapeutic purposes, in particular their use as NO-synthase inhibitors and selective or non selective traps for reactive oxygen species.

Given the potential role of NO and the ROS's in physiopathology, the new derivatives described corresponding to general formula (I) may produce beneficial or favourable effects in the treatment of pathologies where these chemical species are involved. In particular:

- in the treatment of cardiovascular and cerebro-vascular disorders including for example atherosclerosis, migraine, arterial hypertension, septic shock, ischemic or hemorragic cardiac or cerebral infarctions, ischemias and thromboses.
- in the treatment of disorders of the central or peripheral nervous system such as for example neurodegenerative diseases where there can in particular be mentioned cerebral infarctions, sub-arachnoid haemorrhaging, ageing, senile dementias including Alzheimer's disease, Huntington's chorea, Parkinson's disease, Creutzfeld Jacob disease and prion diseases, amyotrophic lateral sclerosis but also pain, cerebral and bone marrow traumas, addiction to opiates, alcohol and addictive substances, erective and reproductive disorders, cognitive disorders, encephalopathies, encephalopathies of viral or toxic origin.
- in the treatment of disorders of the skeletal muscle and neuromuscular joints (myopathy, myosis) as well as cutaneous diseases.
- in the treatment of proliferative and inflammatory diseases such as for example atherosclerosis, pulmonary hypertension, respiratory distress, glomerulonephritis, portal hypertension, psoriasis, arthrosis and rheumatoid arthritis, fibroses, amyloidoses, inflammations of the gastro-intestinal system (colitis, Crohn's disease) or of the pulmonary system and airways (asthma, sinusitis, rhinitis).
- in treatments related to organ transplants.
- in the treatment of auto-immune and viral diseases such as for example lupus, AIDS, parasitic and viral infections, diabetes, multiple sclerosis.
- in the treatment of cancer.
- in the treatment of neurological diseases associated with intoxications (Cadmium poisoning, inhalation of n-hexane, pesticides, herbicides), associated with treatments (radiotherapy) or disorders of genetic origin (Wilson's disease).
- in the treatment of all the pathologies characterized by an excessive production or dysfunction of NO and/or ROS's.

In all these pathologies, there is experimental evidence demonstrating the involvement of NO or ROS's (*J. Med. Chem.* (1995) 38, 4343–4362; *Free Radic. Biol. Med.* (1996) 20, 675–705; *The Neuroscientist* (1997) 3, 327–333).

Furthermore, NO Synthase inhibitors and their use have already been described by the inventors in previous Patents (U.S. Pat. No. 5,081,148; U.S. Pat. No. 5,360,925), as well as the combination of these inhibitors with products having antioxidant or antiradicular properties (Patent Application WO 98/09653). More recently, derivatives of amidines having NO Synthase inhibitory properties and/or antioxidant or antiradicular properties have been described in the Patent Applications WO 98/42696 and WO 98/58934.

The Applicant has now discovered a new class of compounds having an inhibitory activity on NO-synthases and/or an activity which traps the reactive oxygen species (ROS). These compounds, of general formula (I) defined hereafter, are derivatives of 2-aminopyridines.

The compounds according to the invention correspond to general formula (I)

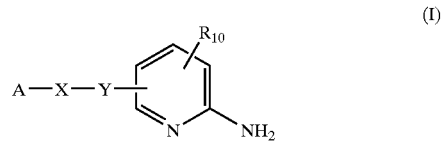

in which A represents a radical which traps free radicals, and in particular:

a radical

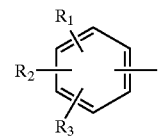

in which $R_1$, $R_2$ and $R_3$ represent, independently, a hydrogen atom, a halogen, the OH or SH group, a linear or branched alkyl, aralkoxy or alkoxy radical having from 1 to 6 carbon atoms, an —O—CO—$R_4$, —$SR_4$, —S(O)$R_4$, —$SO_2R_4$, or —$NR_5R_6$ radical, or also $R_1$ and $R_2$ or $R_2$ and $R_3$ together form a methylenedioxy ring, $R_4$ representing a linear or branched alkyl radical having from 1 to 6 carbon atoms, and $R_5$ and $R_6$ representing independently a hydrogen atom, a linear or branched alkyl radical having from 1 to 6 carbon atoms or an aromatic ring optionally substituted by one or more groups chosen from a halogen atom, the OH group and a linear or branched alkyl or alkoxy radical having from 1 to 6 carbon atoms, or $NR_5R_6$ constitutes a heterocycle with 4 to 6 members, which contains from 1 to 2 heteroatoms chosen from O, S and N, the corresponding members being respectively —O—, —S— and —$NR_7$—, $R_7$ representing a hydrogen atom or a linear or branched alkyl radical having from 1 to 6 carbon atoms, or a radical

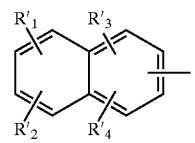

in which $R'_1$, $R'_2$, $R'_3$ and $R'_4$ represent, independently, a hydrogen atom, a halogen, the OH group, or a linear or branched alkoxy radical having from 1 to 6 carbon atoms, or also a radical

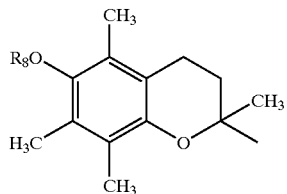

in which $R_8$ represents a hydrogen atom, a linear or branched alkyl radical having from 1 to 6 carbon atoms, a —CO—$R_9$ radical, an arylalkyl radical optionally substituted by one or more linear or branched alkyl or alkoxy radicals having from 1 to 6 carbon atoms, $R_9$ represents a linear or branched alkyl radical having from 1 to 6 carbon atoms;

X represents a —$(CH_2)_m$—, —Q—, —$(CH_2)_m$—CH=CH—Q—, —$(CH_2)_m$—C(=W)—Q—, —$(CH_2)_m$—$NR_{11}$—C(=W)—Q—, —$(CH_2)_m$—$NR_{11}$—C(=W)—O—Q—, —$(CH_2)_m$—$NR_{11}$—C(=W)—$NR_{12}$—Q—, —$(CH_2)_m$—NH—Z—NH—C(=W)—, —$(CH_2)_m$—N=C($R_{16}$)—$NR_{12}$—, —$(CH_2)_m$—CH=CH—C(=W)—Q radical or a linear or branched alkenyl radical having from 1 to 6 carbon atoms, Q representing a bond or a radical chosen from the piperazine, homopiperazine, piperidine, pyrrolidine or azetidine radicals, these radicals can be substituted by one or more linear or branched alkyl radicals having from 1 to 6 carbon atoms, W representing one of the O or S atoms or the NH group, Z representing a phenylene radical optionally substituted by one or more halogen atoms, m being an integer comprised between 0 and 6;

Y represents an alkyl, alkenyl or alkynyl chain, each of these chains can be linear or branched, having up to 10 carbon atoms and be optionally substituted by an $NR_{13}$, $R_{14}$ radical, or Y represents a —$(CH_2)_n$—O—$(CH_2)_p$—, —$(CH_2)_n$—S—$(CH_2)_p$— or —$(CH_2)_n$—$NR_{13}$—$(CH_2)_p$—radical, n and p being integers comprised between 0 and 6;

$R_{10}$ represents a hydrogen atom, one of the OH, CN, $NO_2$ or —$SR_{15}$ radicals, or a linear or branched alkyl or alkoxy radical having from 1 to 6 carbon atoms;

$R_{11}$, $R_{12}$, $R_{13}$, $R_{14}$ and $R_{15}$ represent independently a hydrogen atom or a linear or branched alkyl radical having from 1 to 6 carbon atoms;

$R_{16}$ represents independently a hydrogen atom or a linear or branched alkyl or thioalkyl radical having from 1 to 6 carbon atoms;

It being understood that —X—Y— together do not represent a single bond, a linear or branched alkylene radical or an —O—, —S—, —NH— or —NH—CO—NH-alkylene radical;

it being also understood that when A represents the phenyl radical, —X—Y— together do not represent —NH—CO—NH—;

or a salt of a product of general formula (I).

The compounds of the invention can exist in the state of bases or of addition salts in particular with organic or inorganic acids or with bases, and in particular in the state of hydrates.

By linear or branched alkyl having from 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By linear or branched thioalkyl radicals having from 1 to 6 carbon atoms or linear or branched alkoxy having from 1 to 6 carbon atoms, are meant the thioalkyl or alkoxy radicals, the alkyl radical of which has the meaning indicated previously.

The term aryl refers to a hydrocarbon mono-, di ou tricyclic compound with at least one aromatic ring, each ring containing up to 7 members, such as for example phenyl, naphthyl, anthracyl, biphenyl or indenyl. The aryl radical is optionally substituted by one or more radicals chosen from the group constituted by a halogen atom, an alkyl radical, an alkoxy radical and a nitro radical. The term aralkoxy refers to an alkoxy radical substituted by an aryl radical as defined above.

Preferably, the compounds of general formula (I) as described above will be such that X represents one of the —NH—CO— or —CO—Q— radicals, Q representing one of the piperazine or homopiperazine radicals, these radicals can be substituted by one or more linear or branched alkyl radicals having from 1 to 6 carbon atoms. Furthermore, Y will preferably be chosen as being a —$(CH_2)_n$—$NR_{13}$—$(CH_2)_p$— radical in which $R_{13}$, n and p have the meanings indicated previously.

More preferentially, the compounds of general formula (I) described previously will be chosen such that:

A represents:

a radical

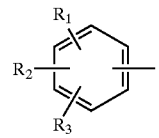

in which $R_1$, $R_2$ and $R_3$ represent, independently, a hydrogen atom, the OH group, a linear or branched alkyl or alkoxy radical having from 1 to 6 carbon atoms or an —$NR_5R_6$ radical, or also $R_1$, and $R_2$ or $R_2$ and $R_3$ together form a methylenedioxy ring, $R_5$ and $R_6$ representing independently a hydrogen atom or a linear or branched alkyl radical having from 1 to 6 carbon atoms, and preferably a hydrogen atom or a methyl or ethyl radical, a 3,5-ditert-butyl-4-hydroxyphenyl or 4-(dimethylamino) phenyl radical, or a radical

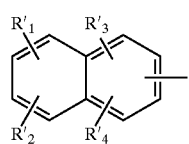

in which $R'_1$, $R'_2$, $R'_3$ and $R'_4$ represent, independently, a hydrogen atom, the OH group, or a linear or branched alkoxy radical having from 1 to 6 carbon atoms, one at least of $R_1$, $R_2$, $R_3$ and $R_4$ preferably representing the OH group, or also a radical

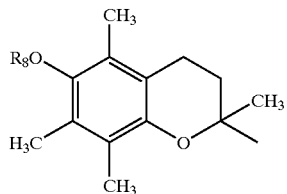

in which $R_8$ represents a hydrogen atom;

X represents one of the —NH—CO— or —CO—Q— radicals, Q representing a piperazine radical optionally substituted by one or two methyl radicals;

Y represents a —$(CH_2)_n$—$NR_{13}$—$(CH_2)_p$— radical in which $R_{13}$ represents a hydrogen atom or a linear or branched alkyl radical having from 1 to 6 carbon atoms and n and p are integers comprised between 0 and 6, or Y represents an alkyl, alkenyl or alkynyl chain, each of these chains can be linear or branched and have up to 10 carbon atoms;

and $R_{10}$ represents a hydrogen atom or a methyl radical.

Quite particularly the following compounds of general formula (I) described in the examples will be preferred:

6-amino-N-[3,5-bis-(1,1-dimethylethyl)-4-hydroxyphenyl]-4-methyl-2-pyridine-pentanamide hydrochloride;

6-amino-N-[3,5-bis-(1,1-dimethylethyl)-4-hydroxyphenyl]-4-methyl-2-pyridine-butanamide hydrochloride;

6-amino-N-[4-(dimethylamino)phenyl]-4-methyl-2-pyridinebutanamide hydrochloride;

1-[4-(2-amino-5-pyridinyl)-3-butynyl]-4-[(3,4-dihydro-6-hydroxy-2,5,7,8-tetramethyl-2H-[1]-benzopyran-2-yl)carbonyl]-piperazine hydrochloride;

1-[4-(2-amino-5-pyridinyl)butyl]-4-[(3,4-dihydro-6-hydroxy-2,5,7,8-tetramethyl-2H-[1]-benzopyran-2-yl)carbonyl]-piperazine hydrochloride;

1-[2-(6-amino-4-methyl-2-pyridinyl)ethyl]-4-[(3,4-dihydro-6-hydroxy-2,5,7,8-tetramethyl-2H-[1]-benzopyran-2-yl)carbonyl]-piperazine hydrochloride;

1-[4-(2-amino-6-pyridinyl)-3-butynyl]-4-[(3,4-dihydro-6-hydroxy-2,5,7,8-tetramethyl-2H-[1]-benzopyran-2-yl)carbonyl]-piperazine hydrochloride;

N-[(6-amino-4-methyl-2-pyridinyl)butyl]-2-hydroxy-5-methoxybenzamide hydrochloride;

N-[(6-amino-4-methyl-2-pyridinyl)butyl]-2,6-dihydroxybenzamide;

N-[(6-amino-4-methyl-2-pyridinyl)butyl]-2,5-dihydroxybenzamide hydrochloride;

5-amino-N-[(6-amino-4-methyl-2-pyridinyl)butyl]-2-hydroxybenzamide hydrochloride;

N-[(6-amino-4-methyl-2-pyridinyl)butyl]-2,5-dihydroxy-3-methylbenzamide hydrochloride;

N-[(6-amino-4-methyl-2-pyridinyl)butyl]-2,5-dihydroxy-3-(1-methylethyl)benzamide;

N-[(6-amino-4-methyl-2-pyridinyl)butyl]-2-hydroxy-4,6-dimethoxy-benzamide hydrochloride;

N-[(6-amino-4-methyl-2-pyridinyl)butyl]-3,5-bis-(1,1-dimethylethyl)-4-hydroxybenzamide hydrochloride;

6-amino-N-[3,5-bis(1,1-dimethylethyl)-4-hydroxyphenyl]-4-methyl-2-pyridineheptanamide hydrochloride;

6-amino-N-[3,5-bis(1,1-dimethylethyl)-4-hydroxyphenyl]-4-methyl-2-pyridinehexanamide hydrochloride;

6-amino-N-[3,5-bis(1,1-dimethylethyl)-4-hydroxyphenyl]-4-methyl-2-pyridineacetamide hydrochloride;

α-amino-N-[4-(dimethylamino)phenyl]-5-(6-amino-2-pyridinyl)-4-pentynamide hydrochloride;

α,6-diamino-N-[4-(dimethylamino)phenyl]-2-pyridinylpentanamide hydrochloride;

6-amino-N-[4-(dimethylamino)phenyl]-4-methyl-2-pyridinehexanamide hydrochloride;

6-amino-N-[4-(dimethylamino)phenyl]-4-methyl-2-pyridineheptanamide hydrochloride;

N-[(6-amino-4-methyl-2-pyridinyl)butyl]-1,3-benzodioxole-5-carboxamide hydrochloride;

6-amino-N-[4-(dimethylamino)phenyl]-4-methyl-2-pyridinepentananamide hydrochloride;

{[4-(6-amino-4-methyl-2-pyridinyl)butyl]amino}-N-[(4-dimethylamino)phenyl]-acetamide hydrochloride;

6-amino-N-[3-(4-hydroxy-3-methoxy-phenyl)-2-propenyl]-4-methyl-2-pyridinebutanamine hydrochloride;

6-amino-N-[4-chloro-2-(phenylamino)phenyl]-4-methyl-2-pyridinepentanamide hydrochloride;

N-[(6-amino-4-methyl-2-pyridinyl)butyl]-1,3-benzodioxole-5-acetamide hydrochloride;

N-[4-(6-amino-4-methyl-2-pyridinyl)butyl]-N-(1,3-benzodioxole-5-ylmethyl)amine fumarate;

N-[4-(6-amino-4-methyl-2-pyridinyl)butyl]-N-[(E)-3-phenyl-2-propenyl]amine fumarate;

(E)-N-[4-(6-amino-4-methyl-2-pyridinyl)butyl]-3-(1,3-benzodioxole-5-yl)-2-propenamide fumarate;

2-({[4-(6-amino-4-methyl-2-pyridinyl)butyl]amino}methyl)-4-methoxyphenol;

N-[2-(benzyloxy)-4,5-dimethoxybenzyl]-4-[6-(2,5-dimethyl-1H-pyrrol-1-yl)-4-methyl-2-pyridinyl]-1-butanamine;

6-(4-{[2-(benzyloxy)-4,5-dimethoxybenzyl]amino}butyl)-4-methyl-2-pyridinamine;

2-({[4-(6-amino-4-methyl-2-pyridinyl)butyl]amino}methyl)-4,5-dimethoxyphenol;

N-[4-(6-amino-4-methyl-2-pyridinyl)butyl]-6-hydroxy-2,5,7,8-tetramethyl-2-chromanecarboxamide fumarate.

More preferably, the products of general formula (I) will be chosen from the group constituted by the following compounds:

6-amino-N-[3,5-bis-(1,1-dimethylethyl)-4-hydroxyphenyl]-4-methyl-2-pyridinepentanamide hydrochloride;

6-amino-N-[4-(dimethylamino)phenyl]-4-methyl-2-pyridinebutanamide hydrochloride;

1-[2-(6-amino-4-methyl-2-pyridinyl)ethyl]-4-[(3,4-dihydro-6-hydroxy-2,5,7,8-tetramethyl-2H-[1]-benzopyran-2-yl)carbonyl]-piperazine hydrochloride;

N-[(6-amino-4-methyl-2-pyridinyl)butyl]-2-hydroxy-5-methoxy-benzamide hydrochloride;

N-[(6-amino-4-methyl-2-pyridinyl)butyl-2,5-dihydroxybenzamide hydrochloride;

N-[(6-amino-4-methyl-2-pyridinyl)butyl]-2,5-dihydroxy-3-methyl-benzamide hydrochloride;

N-[(6-amino-4-methyl-2-pyridinyl)butyl]-2,5-dihydroxy-3-(1-methylethyl)benzamide;

6-amino-N-[4-(dimethylamino)phenyl]-4-methyl-2-pyridinehexanamide hydrochloride;

N-[(6-amino-4-methyl-2-pyridinyl)butyl]-1,3-benzodioxole-5-carboxamide hydrochloride;

6-amino-N-[4-(dimethylamino)phenyl]-4-methyl-2-pyridinepentananamide hydrochloride;

{[4-(6-amino-4-methyl-2-pyridinyl)butyl]amino}-N-[(4-dimethylamino)phenyl]-acetamide hydrochloride;

6-amino-N-[3-(4-hydroxy-3-methoxy-phenyl)-2-propenyl]-4-methyl-2-pyridine-butanamine hydrochloride;

N-[4-(6-amino-4-methyl-2-pyridinyl)butyl]-N-(1,3-benzodioxole-5-ylmethyl)amine fumarate;

N-[4-(6-amino-4-methyl-2-pyridinyl)butyl]-N-[(E)-3-phenyl-2-propenyl]amine fumarate;

(E)-N-[4-(6-amino-4-methyl-2-pyridinyl)butyl]-3-(1,3-benzodioxole-5-yl)-2-propenamide fumarate;

2-({[4-(6-amino-4-methyl-2-pyridinyl)butyl]amino}methyl)-4-methoxyphenol;

6-(4-{[2-(benzyloxy)-4,5-dimethoxybenzyl]amino}butyl)-4-methyl-2-pyridinamine;

2-({[4-(6-amino-4-methyl-2-pyridinyl)butyl]amino}methyl)-4,5-dimethoxyphenol;

N-[4-(6-amino-4-methyl-2-pyridinyl)butyl]-6-hydroxy-2,5,7,8-tetramethyl-2-chromanecarboxamide fumarate.

Yet more preferably, the products of general formula (I) will be chosen from the group constituted by the following compounds:

6-amino-N-[3,5-bis-(1,1-dimethylethyl)-4-hydroxy-phenyl]-4-methyl-2-pyridinepentanamide hydrochloride;

N-[(6-amino-4-methyl-2-pyridinyl)butyl]-2,5-dihydroxy-3-(1-methylethyl)benzamide;

6-amino-N-[4-(dimethylamino)phenyl]-4-methyl-2-pyridinepentananamide hydrochloride;

{[4-(6-amino-4-methyl-2-pyridinyl)butyl]amino}-N-[(4-dimethylamino)phenyl]acetamide hydrochloride;

6-amino-N-[3-(4-hydroxy-3-methoxy-phenyl)-2-propenyl]-4-methyl-2-pyridine-butanamine hydrochloride;

2-({[4-(6-amino-4-methyl-2-pyridinyl)butyl]amino}methyl)-4,5-dimethoxyphenol.

Moreover, the invention offers, as new industrial products, the compounds of general formula (II) and (III)

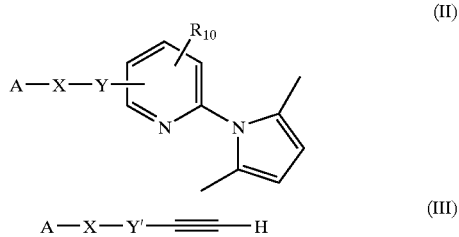

in which A represents a radical which traps free radicals, and in particular:

a radical

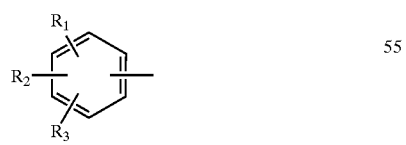

in which $R_1$, $R_2$ and $R_3$ represent, independently, a hydrogen atom, a halogen, the OH or SH group, a linear or branched alkyl, aralkoxy or alkoxy radical having from 1 to 6 carbon atoms, an —O—CO—$R_4$, —$SR_4$, —S(O)$R_4$, —$SO_2R_4$, or —$NR_5R_6$ radical, or also $R_1$ and $R_2$ or $R_2$ and $R_3$ together form a methylenedioxy ring, $R_4$ representing a linear or branched alkyl radical having from 1 to 6 carbon atoms, and $R_5$ and $R_6$ representing independently a hydrogen atom, a linear or branched alkyl radical having from 1 to 6 carbon atoms or an aromatic ring optionally substituted by one or more groups chosen from a halogen atom, the OH group and a linear or branched alkyl or alkoxy radical having from 1 to 6 carbon atoms, or $NR_5R_6$ constitutes a heterocycle with 4 to 6 members, which contains from 1 to 2 heteroatoms chosen from O, S and N, the corresponding members being respectively —O—, —S— and —$NR_7$—, $R_7$ representing a hydrogen atom or a linear or branched alkyl radical having from 1 to 6 carbon atoms or a radical

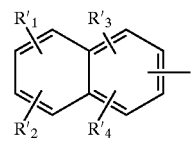

in which $R'_1$, $R'_2$, $R'_3$ and $R'_4$ represent, independently, a hydrogen atom, a halogen, the OH group, or a linear or branched alkoxy radical having from 1 to 6 carbon atoms, or also a radical

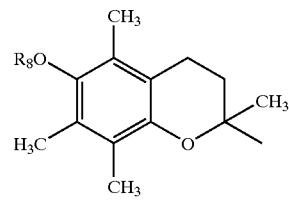

in which $R_8$ represents a hydrogen atom, a linear or branched alkyl radical having from 1 to 6 carbon atoms, a —CO—$R_9$ radical, an arylalkyl radical optionally substituted by one or more linear or branched alkyl or alkoxy radicals having from 1 to 6 carbon atoms, $R_9$ represents a linear or branched alkyl radical having from 1 to 6 carbon atoms;

X represents a —$(CH_2)_m$—Q—, —$(CH_2)_m$—CH=CH—Q—, —$(CH_2)_m$—C(=W)—Q—, —$(CH_2)_m$—$NR_{11}$—C(=W)—Q—, —$(CH_2)_m$—$NR_{11}$—C(=W)—O—Q—, —$(CH_2)_m$—$NR_{11}$—C(=W)—$NR_{12}$—Q—, —$(CH_2)_m$—NH—Z—NH—C(=W)—, —$(CH_2)_m$—N=C($R_{16}$)—$NR_{12}$——$(CH_2)_m$—CH=CH—C(=W)—Q radical or a linear or branched alkenyl radical having from 1 to 6 carbon atoms, Q representing a bond or a radical chosen from the piperazine, homopiperazine, piperidine, pyrrolidine or azetidine radicals, these radicals can be substituted by one or more linear or branched alkyl radicals having from 1 to 6 carbon atoms, W representing one of the O or S atoms or the NH group, Z representing a phenylene radical optionally substituted by one or more halogen atoms, m being an integer comprised between 0 and 6;

Y represents an alkyl, alkenyl or alkynyl chain, each of these chains can be linear or branched, having up to 10 carbon atoms and being optionally substituted by an $NR_{13}R_{14}$ radical, or Y represents a —$(CH_2)_n$—O—$(CH_2)_p$—, —$(CH_2)_n$—S—$(CH_2)_p$— or —$(CH_2)_n$—$NR_{13}$—$(CH_2)_p$— radical, n and p being integers comprised between 0 and 6;

$R_{10}$ represents a hydrogen atom, one of the OH, CN, $NO_2$ or —$SR_{15}$ radicals, or a linear or branched alkyl or alkoxy radical having from 1 to 6 carbon atoms;

$R_{11}$, $R_{12}$, $R_{13}$, $R_{14}$ and $R_{15}$ represent independently a hydrogen atom or a linear or branched alkyl radical having from 1 to 6 carbon atoms;

$R_{16}$ represents independently a hydrogen atom or a linear or branched alkyl or thioalkyl radical having from 1 to 6 carbon atoms;

and Y' represents a a linear or branched alkyl chain having from 1 to 8 carbon atoms;

It being understood that —X—Y— together do not represent a single bond, a linear or branched alkylene radical or an —O—, —S—, —NH— or —NH—CO—NH-alkylene radical;

it being also understood that when A represents the phenyl radical, —X—Y— together do not represent —NH—CO—NH—;

it being finally understood that, for the compound of general formula (III) only, when A represents the phenyl radical, a phenyl radical substituted by one or more halogen atoms or the: naphthyl radical, X does not represent —NH—CO— or —CO—Q'— in which Q' is the piperazine radical.

In certain cases, the compounds according to the present invention (i.e. in particular the compounds of general formulae (I), (II) and (III) described previously) can contain asymmetrical carbon atoms, and therefore have two possible enantiomeric forms, i.e. "R" and "S" configurations The present invention includes the two enantiomeric forms and all combinations of these forms, including "RS" racemic mixtures. In an effort to simplify matters, when no specific configuration is indicated in the structural formulae, it should be understood that the two enantiomeric forms and their mixtures are represented.

A subject of the invention is also, as medicaments, the compounds of general formula (I) described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or inducible NO synthase, to inhibit lipidic peroxidation or to provide the double function of NO synthase inhibition and lipidic peroxidation inhibition.

By pharmaceutically acceptable salt is meant in particular addition salts of inorganic acids such as hydrochloride, sulphate, phosphate, diphosphate, hydrobromide and nitrate, or of organic acids, such as acetate, maleate, fumarate, tartrate, succinate, citrate, lactate, methane sulphonate, p-toluenesulphonate, pamoate, oxalate and stearate. The salts formed: from bases such as sodium or potassium hydroxide also fall within the scope of the present invention, when they can be used. For other examples of pharmaceutically acceptable salts, reference can be made to "Pharmaceutical salts", *J. Pharm. Sci.* 66:1(1977).

The pharmaceutical composition can be in the form of a solid, for example powders, granules, tablets, gelatin capsules, liposomes or suppositories. Appropriate solid supports can be for example calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or glycols, as well as their mixtures, in varying proportions, in water.

A medicament according to the invention can be administered by topical, oral or parenteral route, by intramuscular injection, etc.

The envisaged administration dose for the medicament according to the invention is comprised between 0.1 mg and 10 g according to the type of active compound used.

In accordance with the invention, the compounds of general formula (I) can be prepared by the process described below.

Preparation of Compounds of General Formula (I)

The compounds of general formula (I), in which A, X, Y and $R_{10}$ are as defined above, can be prepared from the intermediates of general formula (II) or the intermediates of general formula (III) and (IV) according to diagram 1.

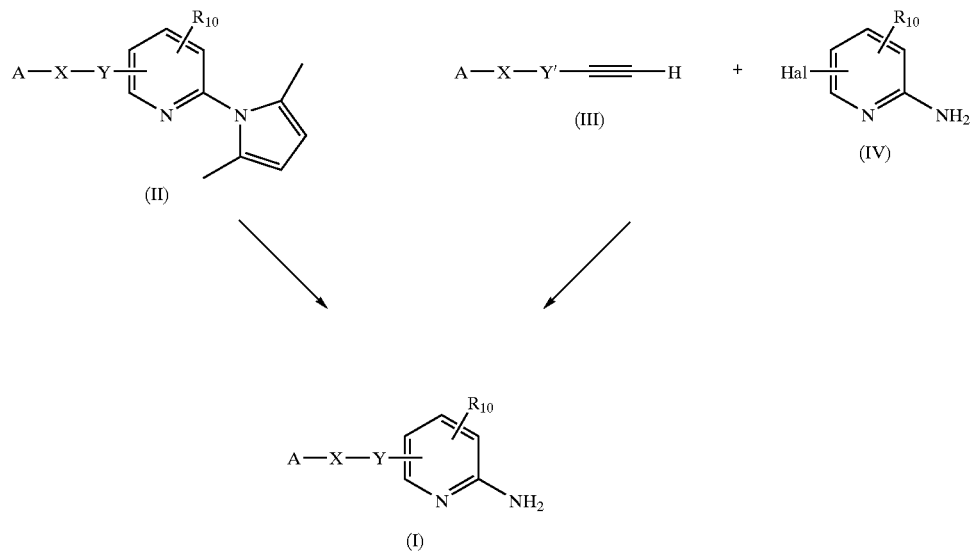

Diagram 1

The final molecules of general formula (I) are obtained after detachment of the protective group 2,5-dimethyl pyrrole from the compounds of general formula (II) by heating in the presence of hydroxylamine hydrochloride, at a temperature which varies from 60° C. to 100° C., in a solvent such as for example ethanol according to an experimental protocol described in *J. Chem. Soc. Perkin Trans.* (1984), 2801–2807.

When the compounds of general formula (I) carry an amine protected by a labile group in acid medium (for example: tert-butyl carbamate$_m$, this is released during the final salification stage carried out, in this case, using a strong acid, in particular HCl.

Alternatively the compounds of general formula (I) can be obtained by heating alkynes of general formula (III) with the halogeno-pyridine intermediates of general formula (IV), either in the presence of Palladium(0) derivatives, such as Pd(PPh3)4 operating under an inert atmosphere in n-butylamine, or in the presence of a Palladium (II) derivative, such as Pd(OAc)$_2$, and PPh$_3$ in piperidine (*J. Med. Chem.*, (1996), 36 (16), 3179–3187). The acetylenic derivatives of general formula (I) thus obtained can be optionally converted into ethylenic derivatives by reduction either under a hydrogen atmosphere in the presence of a catalyst of Lindlar type or by reduction in the presence of a hydride such as RedA1 (*J. Org. Chem.*, (1988), 53, 3845). The acetylenic compounds of general formula (I) can also be reduced by Pd/C under a hydrogen atmosphere in an alcoholic solvent such as ethanol in order to directly lead to the corresponding alkanes.

When the compounds of general formula (III) carry a protected amine (principally in the form of tert-butyl carbamate), this is released after condensation (III)+(IV) during the final salification stage of the molecules in the presence of a strong acid (for example HCl).

Preparation of Compounds of General Formula (II), (III) and (IV)

A) The Compounds of General Formula (II) Can be Prepared According to the Following Methods:

The synthetic precursors which lead to the intermediates of general formula (II) are prepared from compounds of general formula (II.1), such as for example 2-(2,5-dimethylpyrrol-1-yl)-4,6-dimethylpyridine. This is obtained from commercial 6-amino-2,4-lutidine according to an experimental protocol described in *J. Chem. Soc. Perkin Trans.*, (1984), 12, 2801–2807. Treatment of the compounds of general formula (II.1) by a strong base such as, for example, nBuLi, at a temperature which varies from −50° C. to −30° C. in an anhydrous solvent such as ethyl ether, under an inert atmosphere and optionally in the presence of N,N,N',N'-tetramethylethylenediamine allows the formation of the lithiated derivative (intermediate (II.2)) which in the presence of an electrophile E$^+$ leads to the adducts of general formula (II.X).

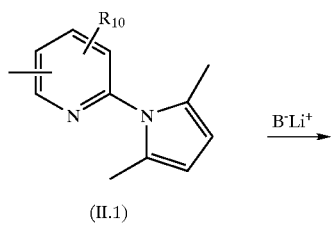

(II.1)

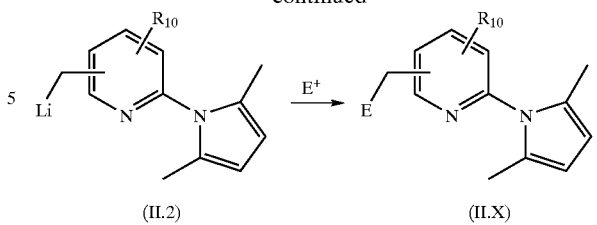

(II.2)     (II.X)

Among the electrophiles E$^+$ which can react on the lithiated type of general formula (II.2), there can be mentioned for example $CO_2$, halogeno-esters, halogeno-orthoesters, paraformaldehyde, protected halogeno-alcohols (for example in the form of tetrahydropyrane acetal) or protected halogeno-amines.

1) Methods of Accessing Substituted 2-(2.5-Dimethylpyrrol-1-yl)pyridines of General Formula (II.X)

1.1) Preparation of Alcohols of General Formula (II.3):

The action of the derivative (II.2) on paraformaldehyde or on protected halogeno-alcohols allows access, after optional deprotection, to the alcohols of general formula (II.3), in which Y and R$_{10}$ are as defined above.

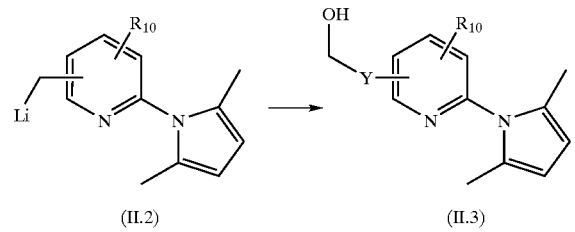

(II.2)     (II.3)

1.2) Preparation of Aldehydes of General Formula (II.4)

The aldehydes of general formula (II.4), in which Y and R$_{10}$ are as defined above, can be prepared by oxidation of the alcohols of general formula (II.3) and by using, for example oxalyl chloride in DMSO (Swern oxidation) or a pyridine-sulphurtrioxide complex in the presence of a base such as triethylamine (*Tetrahedron Lett.*, (1982), 23, 807):

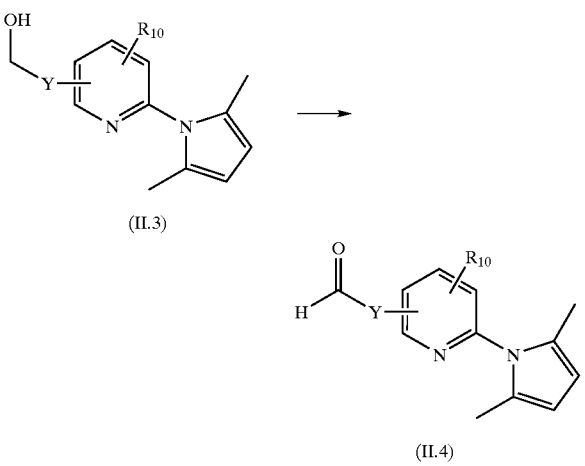

(II.3)

(II.4)

Or these aldehydes are also accessible by the condensation of the intermediates of general formula (II.2) with the derivatives of halogeno-acetal type followed by a standard deprotection stage in an acid medium:

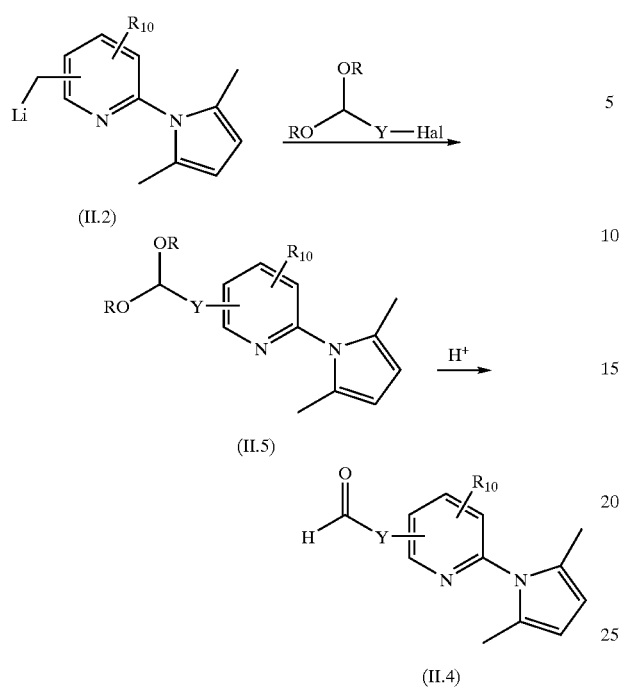

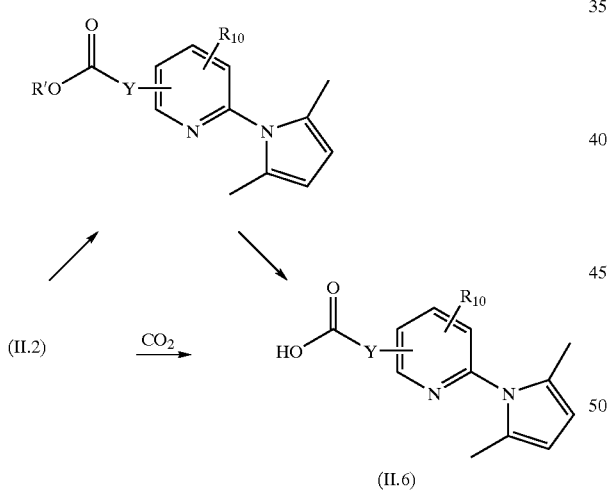

1.3) Preparation of Carboxylic Acids of General Formula (II.6):

The action of the intermediate (II.2) on $CO_2$ and on the halogeno-ester or orthoester derivatives allows access, after optional deprotection, to the carboxylic acids of general formula (II.6), in which Y and $R_{10}$ are as defined above:

These acids can also be obtained by the oxidation of aldehydes of general formula (II.4) by silver nitrate according to an experimental protocol described in *J. Org. Chem.*, (1985), 50, 2981–2987.

1.4) Preparation of Amines of General Formula (II.7):

The alcohols of general formula (II.3), described previously, allow access to amines of general formula (II.7) in which Q, Y and $R_{10}$, are as defined above. The alcohol function is activated fin a standard fashion in the form of a sulphonate derivative of general formula (II.8) before being displaced by an amine and in particular a heterocyclic amine. Condensation is carried out in the presence of Caesium carbonate and LiI at a temperature of 70° C. to 100° C. and in particular under reflux of butanone. The heterocycles such as piperazine are used in mono-protected form (e.g. Boc) during the condensation and an additional selective deprotection is then necessary in order to release the second amine function:

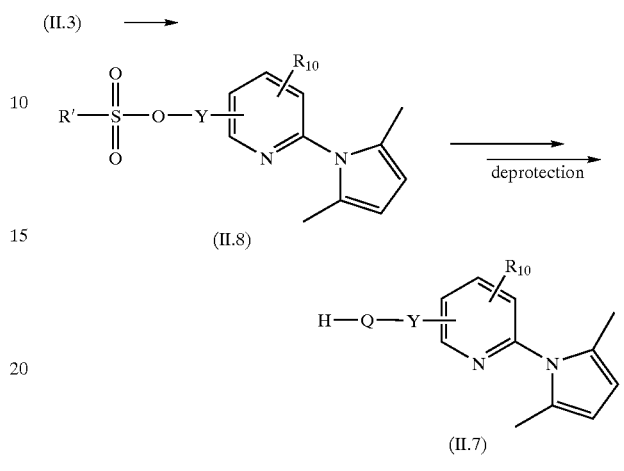

In the particular case where Q is a single bond and $Y=-HN(R_{13})-(CH_2)_p-$, the amines of general formula (II.7) are prepared from intermediate (II.2) which is condensed on protected halogeno-amines (for example in the form of silylated or phthalimide derivatives) under the conditions described previously. The primary amines of general formula (II.7) are finally obtained after deprotection under the conditions described in the literature (T. W. Greene and P. G. M. Wuts, Protective Groups in Organic Synthesis, Second edition (Wiley-Interscience, 1991)).

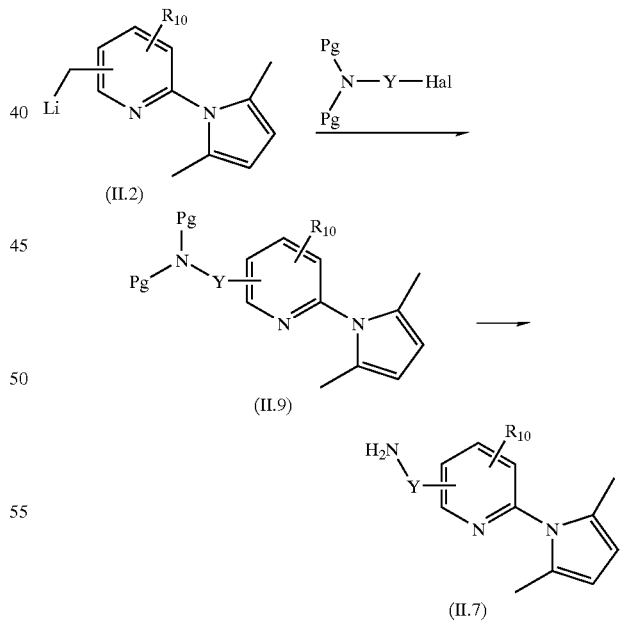

2) Methods of Accessing the Compounds of General Formula (II)

2.1) Carboxamides of General Formula (II):

2.1.1) The carboxamides of general formula (II), in which A, X, Y and $R_{10}$ are as defined above, are prepared by condensation of the amines of general formula (A.1) with the acids of general formula (II.6), described previously, according to the standard methods used in peptide condensation (M. Bodanszky and A. Bodanszky, The Practice of Peptide Synthesis (Springer-Verlag, 1984)). The synthesis of the non-commercial amines of general formula (A.1), is described further on.

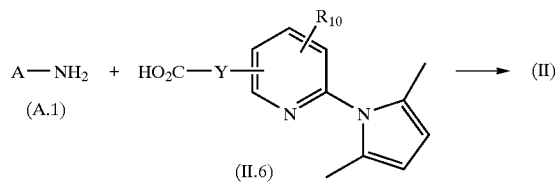

2.1.2) The carboxamides of general formula (II), in which A, X, Y and $R_{10}$ are as defined above, can also be prepared by condensation of the carboxylic acids of general formula (A.2) with the amines of general formula (II.7) under the conditions described previously. The synthesis of the non commercial carboxylic acids of general formula (A.2), is described further on.

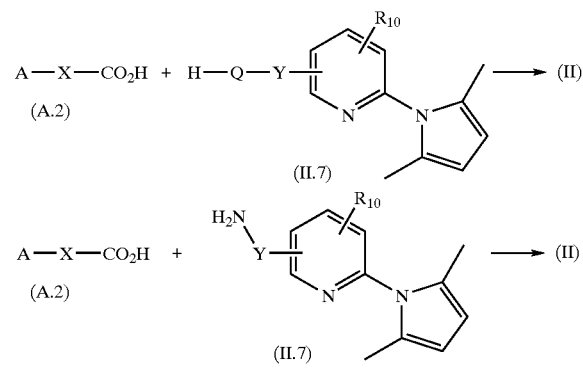

2.2) Amines of General Formula (II):

2.2.1) The amines of general formula (II), in which A, X, Y and $R_{10}$ are as defined above, are prepared by condensation of an amine of general formula (A.1) or (A.3) with an aldehyde of general formula (II.4) during a reducing amination stage in the presence of a reducing agent, such as for example sodium borohydride or sodium triacetoxyborohydride and in a solvent such as, for example, 1,2-dichloroethane. The synthesis of the amines of general formula (A.3) is described further on.

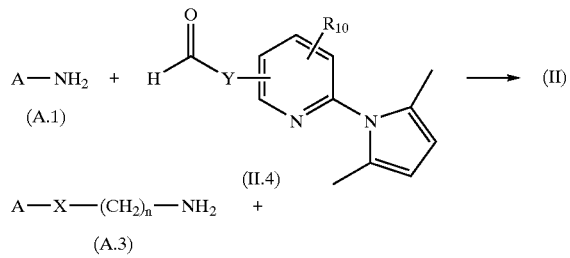

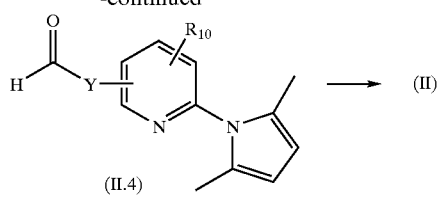

2.2.2) The amines of general formula (II), in which A, X, Y and $R_{10}$ are as defined above, can also be prepared by condensation of the aldehydes of general formula (A.4) or the cinnamaldehyde derivatives of general formula (A.5) with the amines of general formula (II.7) under the conditions described previously:

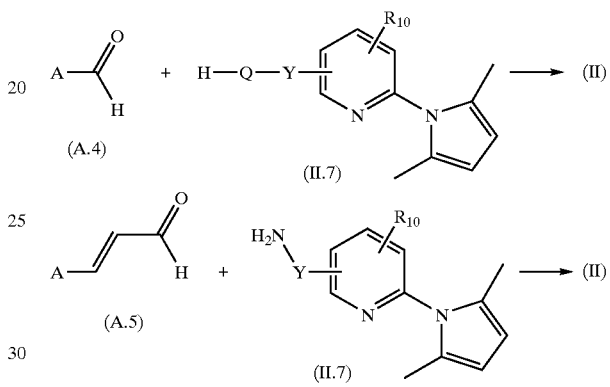

3) Methods of Accessing the Intermediates of General Formula (A.X)

3.1) Synthesis of the Amines of General Formula (A.1):

In the particular case where A is a phenolic derivative, the anilines of general formula (A.1) are obtained by hydrogenation, in the presence of a catalytic quantity of Pd/C, of the corresponding nitrophenol derivatives, themselves synthesized according to a method described in the literature (*J. Org. Chem.*, (1968), 33 (1), 223–226). The amino-diphenylamines of general formula (A.1) are accessible from methods described in the literature (*Synthesis* (1990) 430; *Indian J. Chem.* (1981) 20B, 611–613; *J. Med. Chem.* (1975) 18(4), 386–391). The nitro-diphenylamines obtained in an intermediate fashion lead, either by catalytic hydrogenation, or by using $SnCl_2$ (*J. Heterocyclic Chem.* (1987), 24, 927–930; *Tetrahedron Letters* (1984), 25, (8), 839–842) to the amino-diphenylamines of general formula (A.1).

3.2) Synthesis of the Carboxylic Acids of General Formula (A.2):

The carboxylic acids of general formula (A.2) can be prepared according to the methods described in the literature: *Can. J. Chem.* (1972), 50, 1276–1282, *J. Org. Chem.* (1961) 26, 1221–1223 or *Acta Chem. Scandinavica* (1973) 27, 888–890.

3.3) Synthesis of the Amines of General Formula (A.3):

The amines of general formula (A.3), in which A, X and n are as described previously, are prepared, in two stages, by condensation of the amines of general formula (A.1) with the commercial protected amino acids, of general formula (A.6) under standard conditions of peptide synthesis described previously. Deprotection of the terminal amine of the intermediate of general formula (A.7) is then carried out during the last stage, and for example in a strong acid medium in order to detach the tert-butoxycarbonyl function:

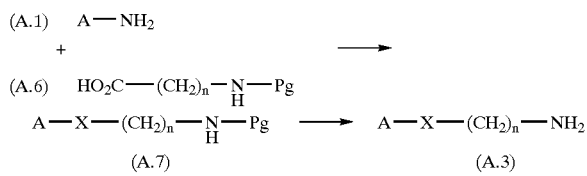

B) The Compounds of General Formula (III) can be prepared according to the following methods:

The acetylenic compounds of general formula (III), in which A, Q, W, Y and m are as defined above, are prepared by nucleophilic substitution of the commercial acetylenic derivatives of general formula (B.1), in which Gp is a labile group such as halogen or sulphonic derivatives, by an amine of general formula (B.2) according to a procedure described in *J. Med. Chem.*, (1996), 39 (16), 3179–3187.

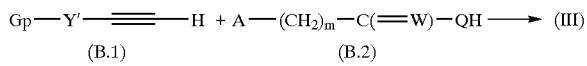

The amines of general formula (B.2) are easily accessible from methods described in the literature (e.g.: *J. Med. Chem.*, (1992), 35 (23), 4464–4472).

C) The Compounds of General Formula (IV) Can be Prepared According to the Following Methods:

The non-commercial halogenated derivatives of 2-aminopyridine of general formula (IV), in which $R_{10}$ is as defined above, can be prepared according to methods described in the literature and in particular those described in *J. Org. Chem.*, (1962), 27, 2473–2478, *Rec Trav. Chim.*, (1966), 85, 803 or *Aust. J. Chem.*, (1982), 25, 2025–2034.

Unless they are defined differently, all the technical and scientific terms used here have the same meaning as that usually understood by an ordinary specialist in the field to which the invention belongs. Similarly, all publications, patent applications, patents and other references mentioned here are incorporated by way of reference.

The following examples are presented to illustrate the above procedures and should in no way be considered as limiting the scope of the invention.

EXAMPLES

Example 1

6-amino-N-[3,5-bis-(1,1-dimethylethyl)-4-hydroxyphenyl]-4-methyl-2-pyridinepentanamide hydrochloride: 1

1.1) methyl 6-(2,5-dimethylpyrrol-1-yl)-4-methyl-2-pyridinepentanoate:

0.4 g (2 mmoles) of 2-(2,5-dimethylpyrrol-1-yl)-4,6-dimethylpyridine (prepared from 6-amino-2,4-lutidine according to *J. Chem. Soc. Perkin Trans.* (1984), 12, 2801–2807) is dissolved in 5 ml of anhydrous ethyl ether under an argon atmosphere. The reaction mixture is cooled down to −25° C. and 0.9 ml (2.2 mmoles) of a 2.5M solution of BuLi in hexane is added dropwise. After 10 minutes at −25° C., 0.35 ml (2 mmoles) of trimethyl 4-bromobutyrate is added. After having left the temperature to return slowly to 23° C. overnight, 10 ml of a saturated solution of ammonium chloride is added to the reaction mixture and finally dilution is carried out with 10 ml of ethyl acetate. The organic phase is decanted and washed successively with 10 ml of water and 10 ml of salt water, dried over sodium sulphate, filtered and concentrated under vacuum. The residue obtained is purified on a silica column (eluant: heptane/ethyl acetate: 95/5) in order to produce a yellow oil with a yield of 55%.

NMR $^1$H (CDCl$_3$, 400 MHz, δ): 1.70 (m, 2H, CH$_2$); 1.80 (m, 2H, CH$_2$); 2.10 (s, 6H, 2CH$_3$ pyrrole); 2.35 (m, 5H, CH$_2$+CH$_3$); 2.80 (m, 2H, CH$_2$); 3.65 (s, 3H, O—CH$_3$); 5.90 (s, 2H, pyrrole); 6.85 (s, 1H, pyridine); 6.95 (s, 1H, pyridine).

1.2) 6-(2,5-dimethylpyrrol-1-yl)-4-methyl-2-pyridinepentanoic acid:

A solution of 0.37 g (6.6 mmoles) of KOH in 10 ml of a water/methanol mixture (1/1) is added dropwise to a solution of 0.98 g (3.3 mmoles) of intermediate 1.1 in 10 ml of methanol. The whole is agitated for 15 hours at 23° C. and finally diluted with 20 ml of ethyl acetate. After decanting, the aqueous phase is washed with 20 ml of ethyl acetate and then acidified cold with a 2M solution of hydrochloric acid. The product is then extracted twice with 20 ml of ethyl acetate. After drying over sodium sulphate and filtration, the organic solution is concentrated under vacuum. The evaporation residue is purified on a silica column (eluant: heptane/ethyl acetate: 7/3). The expected product is obtained in the form of a colourless oil with a yield of 64%.

NMR $^1$H (CDCl$_3$, 400 MHz, δ): 1.70 (m, 2H, CH$_2$); 1.85 (m, 2H, CH$_2$); 2.10 (s, 6H, 2 CH$_3$ pyrrole); 2.40 (m, 5H, CH$_2$+CH$_3$); 2.80 (m, 2H, CH$_2$); 5.90 (s, 2H, pyrrole); 6.85 (s, 1H, pyridine); 7.00 (s, 1H, pyridine).

1.3) 2,6-di-t-butyl-4-nitrophenol:

2,6-di-t-butylphenol (8 g, 39 mmoles) is dissolved in 25 ml of cyclohexane at 10° C. A mixture (1/1) of nitric acid/acetic acid (5 ml) is added dropwise to the reaction medium maintained at this temperature. Then agitation is carried out for 15 minutes at ambient temperature, then the precipitate formed is filtered, followed by rinsing with water and with pentane. The 2,6-di-t-butyl-4-nitrophenol obtained (6.34 g, 65%) is dried in an oven and will be used without other purification in the following stages. Pale yellow powder. Melting point: 167–168° C.

NMR $^1$H (CDCl$_3$, 100 MHz, δ): 1.48 (s, 18H, 2tBu); 5.93 (s, 1H, OH); 8.13 (s, 2H, arom H.).

1.4) 2,6-di-t-butyl-4-aminophenol:

2,6-di-t-butyl-4-nitrophenol (6.3 g, 25 mmoles) is dissolved in methanol (100 ml). 0.6 g of palladium on carbon (10%) is added and the whole is placed under a hydrogen atmosphere under 2 bars of pressure. The catalyst is filtered out and the solvent is evaporated off under reduced pressure. The residue is taken up in heptane and filtered. In this way 2,6-di-t-butyl-4-aminophenol (2.7 g, 48%) is obtained which will be used without other purification in the following stages. Pink powder. Melting point: 123–124° C.

NMR $^1$H (CDCl$_3$, 100MHz, δ): 6.60 (s, 2H, Ph); 4.65 (broad s, 1H, OH); 3.15 (broad s, 2H, NH$_2$); 1.42 (s, 18H, 2×tBu).

1.5) N-[3,5-bis-(1,1-dimethylethyl)-4-hydroxyphenyl]-6-(2,5-dimethylpyrrol-1-yl)-4-methyl-2-pyridinepentanamide:

0.47 g (2.27 mmoles) of 1,3-dicyclohexylcarbodiimide is added in one portion to a solution of 0.59 g (2.06 mmoles) of intermediate 1.2, 0.46 g (2.06 mmoles) of 2,6-di-t-butyl-4-aminophenol and 0.31 g (2.27 mmoles) of hydroxybenzotriazole in 20 ml of dichloromethane. The reaction mixture is agitated overnight at 23° C., the precipitate formed is filtered and the filtrate is concentrated to dryness under vacuum. The residue is dissolved in 20 ml of ethyl acetate and washed successively with 20 ml of water and with 20 ml of salt water. The organic solution is dried over sodium sulphate, filtered, concentrated under vacuum and the evaporation residue is purified on a silica column (eluant: dichloromethane/methanol: 98/2). The pure fractions are collected and evaporated under vacuum in order to produce a transparent oil with a yield of 39%.

NMR $^1$H (DMSO d6, 400 MHz, δ): 1.35 (s, 18H, 2 tBu); 1.60 (m, 2H, CH$_2$); 1.70 (m, 2H, CH$_2$); 2.00 (s, 6H, 2 CH$_3$ pyrrole); 2.25 (m, 2H, CH$_2$); 2.35 (s, 3H, CH$_3$); 2.70 (m, 2H, CH$_2$); 5.75 (s, 2H, pyrrole); 6.70 (s, 1H, OH); 7.00 (s, 1H, pyridine); 7.10 (s, 1H, pyridine); 7.35 (s, 2H, Ph); 9.55 (s, 1H, CO—NH).

1.6) 6-amino-N-[3,5-bis-(1,1-dimethylethyl)-4-hydroxyphenyl]-4-methyl-2-pyridine-pentanamide hydrochloride:

Intermediate 1.5 (0.43 g, 0.88 mmole) is dissolved in 9 ml of ethanol with 3 ml of water added to it and 0.31 g (4.40 mmoles) of hydroxylamine hydrochloride is added. The reaction mixture is heated under reflux for 24 hours. After returning to 22° C., the whole is diluted with 10 ml of a saturated solution of sodium bicarbonate and the product is extracted with 20 ml of ethyl acetate. After decanting, the organic solution is washed successively with 20 ml of a saturated solution of sodium bicarbonate and with 10 ml of salt water, dried over sodium sulphate, filtered and concentrated under vacuum. The evaporation residue is taken up in ethyl ether and filtered in order to produce the free base in the form of a beige solid with a yield of 76%. The product is then salified by treatment of 0.27 g (0.67 mmole) of the free base in solution in 5 ml of dry methanol with 2.68 ml (2.68 mmoles) of an anhydrous 1N solution of HCl in ethyl ether. A beige powder is obtained. Melting point: 162–164° C.

NMR $^1$H (DMSO d6, 400 MHz, δ): 1.35 (s, 18H, 2 tBu); 1.50–1.80 (m, 4H, 2 CH$_2$); 2.30 (s, 5H, CH$_2$+CH$_3$); 2.70 (m, 2H, CH$_2$); 6.60 (s, 2H, pyridine); 6.70 (s, 1H, OH); 7.40 (s, 2H, Ph); 7.75 (broad s, 2H, NH$_2$); 9.66 (s, 1H, CO—NH); 13.95 (broad s, 1H, NH$^+$).

IR: $v_{C=O}$ (amide): 1657 cm$^{-1}$.

Example 2

6-amino-N-13,5-bis-(1,1-dimethylethyl)-4-hydroxyphenyl]4-methyl-2-pyridinebutanamide hydrochloride: 2

2.1) 6-(2,5-dimethylpyrrol-1-yl)-4-methyl-2-{4-[(3,4,5,6-tetrahydro-2H-pyran-2-yl)oxy]butyl}-pyridine:

In a three-necked flask, under an argon atmosphere, 2 g (10 mmoles) of 2-(2,5-dimethyl-pyrrol-1-yl)-4,6-dimethylpyridine is dissolved in 15 ml of anhydrous ethyl ether to which a catalytic quantity of NaI is added. The reaction medium is cooled down to −25° C. before the dropwise addition of 4.4 ml (11 mmoles) of a 2.5M solution of BuLi in hexane, followed 15 minutes later by 1.65 ml (10 mmoles) of 2-(3-chloropropoxy)tetrahydro-2H-pyrane. After agitation for 10 minutes at −25° C., the temperature of the reaction medium is left to slowly return to 23° C. overnight. The reaction medium is finally diluted with 20 ml of a saturated solution of ammonium chloride followed by 30 ml of ethyl acetate. After decanting, the aqueous phase is reextracted with 20 ml of ethyl acetate, the organic phases are then collected and washed successively with 30 ml of water and with 20 ml of salt water. The organic solution is dried over sodium sulphate, filtered and concentrated under vacuum. The evaporation residue is purified on a silica column (eluant: heptane/ethyl acetate: 9/1). The expected product is obtained in the form of a pale yellow oil with a yield of 82%.

NMR $^1$H (CDCl$_3$, 400 MHz, δ): 1.51–1.85 (m, 10H, 5 CH$_2$); 2.11 (s, 6H, 2 CH$_3$ pyrrole); 2.38 (s, 3H,; CH$_3$); 2.80 (t, 2H, CH$_2$, J=7.64 Hz); 3.46 (m, 2H, CH$_2$); 3.80 (m, 2H, CH$_2$); 4.57 (m, 1H, CH—O); 5.87 (s, 2H, pyrrole); 6.84 (s, 1H, pyridine); 6.97 (s, 1H, pyridine).

2.2) 6-(2,5-dimethylpyrrol-1-yl)-4-methyl-2-pyridinebutanol:

2.08 g (6.07 mmoles) of intermediate 2.1 is dissolved in 10 ml (12.1 mmoles) of a 5% solution of HCl in methanol. After agitation for 2 hours at 23° C., the reaction mixture is neutralized by the addition of a saturated solution of NaHCO$_3$, then partially concentrated under vacuum and finally diluted with 30 ml of ethyl acetate. The organic phase is decanted, washed with 20 ml of water followed by 10 ml of salt water, dried over sodium sulphate, filtered and concentrated under vacuum. The evaporation residue is purified on a silica column (eluant: heptane/ethyl acetate: 6/4). The pure fractions are collected and evaporated in order to produce a colourless oil with a yield of 77%.

NMR $^1$H (CDCl$_3$, 400 MHz, δ): 1.60 (m, 2H, CH$_2$); 1.83 (m, 2H, CH$_2$); 2.11 (s, 6H, 2 CH$_3$ pyrrole); 2.39 (s, 3H, CH$_3$); 2.81 (t, 2H, CH$_2$, J=7.63 Hz); 3.64 (t, 2H, CH$_2$, J=6.38 Hz); 5.88 (s, 2H, pyrrole); 6.86 (s, 1H, pyridine); 6.99 (s, 1H, pyridine).

2.3) 6-(2,5-dimethylpyrrol-1-yl)-4-methyl-2-pyridinebutanal:

1.3 ml (9.2 mmoles) of triethylamine and a solution of 0.74 g (4.6 mmoles) of sulphurtrioxide-pyridine complex in 5 ml of DMSO are added successively to a solution of 0.4 g (1.54 mmole) of intermediate 2.2 in 5 ml of DMSO. At the end of one hour of agitation at 30° C., the reaction mixture is poured into 50 ml of water and the product is extracted with 20 ml of ethyl acetate. After decanting, the organic phase is washed with 20 ml of water followed by 10 ml of salt water, dried over sodium sulphate, filtered and finally concentrated to dryness under vacuum. The residue is purified on a silica column (eluant: heptane/ethyl acetate: 8/2), the pure fractions are collected and evaporated under vacuum in order to produce a colourless oil with a yield of 70%.

NMR $^1$H (DMSO d6, 400 MHz, δ): 2.40 (m, 2H, CH$_2$); 2.50 (s, 6H, 2 CH pyrrole); 2.83 (s, 3H, CH$_3$); 2.93 (m, 2H, CH$_3$); 3.18 (t, 2H, CH$_3$, J=7.36 Hz); 6.23 (s, 2H, pyrrole); 7.52 (s, 1H, pyridine); 7.60 (s, 1H, pyridine); 10.12 (s, 1H, CHO).

2.4) 6-(2,5-dimethylpyrrol-1-yl)-4-methyl-2-pyridinebutanoic acid:

A solution of 1.02 g (5.95 mmoles) of AgNO$_3$ in 4 ml of water and dropwise a solution of 1.73 g (31 mmoles) of KOH in 30 ml of water are added successively to a solution of 0.61 g (2.38 mmoles) of intermediate 2.3 in 20 ml of ethanol. A black precipitate forms rapidly and the reaction mixture is agitated for 3 hours at 22° C. The reaction mixture is filtered and the filtrate is acidified with a molar solution of HCl until the pH=3. The aqueous solution is extracted with 3 times 20 ml of dichloromethane, the organic phases are collected, filtered on paper and the filtrate is washed twice with 20 ml of salt water. The organic solution is dried over sodium sulphate, filtered and concentrated under vacuum. A dark yellow oil is obtained with a yield of 92%. The product is used as it is in the following reaction.

2.5) N-[3,5-bis-(1,1-dimethylethyl)-4-hydroxyphenyl]-6-(2,5-dimethylpyrrol-1-yl)-4-methyl-2-pyridinebutanamide:

The experimental protocol used is the same as that described for intermediate 1.5, intermediate 2.4 replacing intermediate 1.4. The expected product is obtained in the form of a white powder with a yield of 41%. Melting point=78–80° C.

NMR $^1$H (DMSO d6, 400 MHz, δ): 1.34 (s, 18H, 2 tBu); 1.97 (m, 2H, CH$_2$); 2.04 (s, 6H, 2 CH$_3$ pyrrole); 2.27 (m, 2H, CH$_2$); 2.35 (s, 3H, CH$_3$); 2.73 (m, 2H, CH$_2$); 5.76 (s, 2H, pyrrole); 6.71 (s, 1H, OH); 7.04 (s, 1H, pyridine); 7.13 (s, 1H, pyridine); 7.38 (s, 2H, Ph); 9.56 (s, 1H, CO—NH).

2.6) 6-amino-N-[3,5-bis-(1,1-dimethylethyl)-4-hydroxyphenyl]-4-methyl-2-pyridinebutanamide hydrochloride:

The experimental protocol used is the same as that described for intermediate 1.6, intermediate 2.5 replacing intermediate 1.5. After salification of the free base under the conditions described previously, the hydrochloride is obtained in the form of a mauve powder with a yield of 56%. Melting point: 164–166° C.

NMR $^1$H (DMSO d6, 400 MHz, δ): 1.34 (s, 18H, 2 tBu), 1.96 (m, 2H, CH$_2$), 2.24 (s, 3H, CH$_3$), 2.28 (m, 2H, CH$_2$), 2.68 (m, 2H, CH$_2$), 6.57 (s, 1H, pyridine), 6.60 (s, 1H, pyridine), 6.75 (s, 1H, OH), 7.38 (s, 2H, Ph), 7.80 (broad s, 2H, NH$_2$), 9.69 (s, 1H, CO—NH), 13.93 (broad s, 1H, NH+).

IR: $\nu_{C=O}$ (amide): 1662 cm$^{-1}$.

Example 3

6-amino-N-[4-(dimethylamino)phenyl]-4-methyl-2-pyridinebutanamide hydrochloride: 3

3.1) N-[4-(dimethylamino)phenyl]-6-(2,5-dimethylpyrrol-1-yl)-4-methyl-2-pyridinebutanamide:

The experimental protocol used to condense N,N-dimethyl-p-phenylenediamine with intermediate 2.4 is the same as that described for the synthesis of intermediate 1.5. The expected product is obtained in the form of a violet oil with a yield of 52%.

NMR $^1$H (CDCl$_3$, 400 MHz, δ): 2.11 (s, 6H, 2 CH$_3$ pyrrole); 2.14 (m, 2H, CH$_2$); 2.35(m, 2H, CH$_2$); 2.42 (s, 3H, CH$_3$); 2.90 (m, 8H, N(CH$_3$)$_2$+CH$_2$); 5.92 (s, 2H, pyrrole); 6.66 (m, 2H, Ph); 6.94 (s, 1H, pyridine); 7.06 (s, 1H, pyridine); 7.27 (m, 2H, Ph); 8.44 (s, 1H, CO—NH).

3.2) 6-amino-N-[4-(dimethylamino)phenyl]-4-methyl-2-pyridinebutanamide hydrochloride:

The experimental protocol used is the same as that described for intermediate 1.6, intermediate 3.1 replacing intermediate 1.5. A beige powder is obtained with a yield of 28%. Melting point: 158–160° C.

NMR $^1$H (DMSO d6, 400 MHz, δ): 2.00 (m, 2H, CH$_2$); 2.26 (s, 3H, CH$_3$); 2.40 (m, 2H, CH$_2$); 2.70 (m, 2H, CH$_2$); 3.06 (m, 6H, N(CH$_3$)$_2$); 6.60 (m, 2H, Ph); 7.75 (m, 6H, Ph+pyridine+NH$_2$); 10.4 (s, 1H, CO—NH); 13.30 (broad s, 1H, NH$^+$); 14.05 (broad s, 1H, NH$^+$).

IR: $\nu_{C=O}$ (amide): 1661 cm$^{-1}$.

Example 4

1-[4(2-amino-5-pyridinyl)-3-butynyl]-4-[(3,4-dihydro-6-hydroxy-2,5,7,8-tetramethyl-2H-[1]-benzopyran-2-yl)carbonyl]-piperazine hydrochloride: 4

4.1) 1-(3-butynyl)-4-[(3,4-dihydro-6-hydroxy-2,5,7,8-tetramethyl-2H-[1]-benzopyran-2-yl)carbonyl]-piperazine:

0.64 g (2 mmoles) of [(3,4-dihydro-6-hydroxy-2,5,7,8-tetramethyl-2H-[1]-benzopyran-2-yl)carbonyl]-piperazine (J. Med. Chem., (1992), 35 (23), 4464–4472), 0.49 g (2.19 mmoles) of 3-butynyl p-toluenesulphonate and 0.18 g (2.19 mmoles) of powdered NaHCO$_3$ are: introduced successively into a flask containing 15 ml of DMF. The reaction mixture is heated at 70° C. for 16 hours. After cooling down, the reaction medium is diluted with 100 ml of water and 80 ml of dichloromethane. The organic phase is decanted and washed 3 times with 50 ml of water, with 50 ml of salt water, dried over: sodium sulphate, filtered and finally concentrated under vacuum. The evaporation residue is purified on a silica column (eluant: heptane/ethyl acetate: 1/3). A white powder is obtained with a yield of 69%. Melting point: 150–152° C.

4.2) 1-[4-(2-amino-5-pyridinyl)-3-butynyl]-4-[(3,4-dihydro-6-hydroxy-2,5,7,8-tetramethyl-2H-[1]-benzopyran-2-yl)carbonyl]-piperazine hydrochloride:

A solution of 0.24 g (1.35 mmole) of 2-amino-5-bromo-pyridine and 0.50 g (1.35 mmole) of intermediate 4.1 in 10 ml of n-butylamine is degassed for 30 minutes using a flow of argon before the addition of 0.096 g (0.083 mmole) of Pd(PPh$_3$)$_4$. The reaction mixture is then heated for 16 hours under an argon atmosphere. After concentration to dryness under vacuum, the residue is taken up in 100 ml of a 1/1 mixture of dichloromethane and water. The organic phase is decanted, washed successively with twice 50 ml of water, with 50 ml of salt water, dried over sodium sulphate, filtered and concentrated under vacuum. The residue is purified on a silica column (eluant: dichloromethane/ethanol: 15/1). The free base is obtained in the form of a yellow powder with a yield of 48%.

Then 0.15 g (0.32 mmole) of the free base is dissolved in 7 ml of dry ethanol and the solution is cooled down using an ice bath before the dropwise addition of 1.3 ml of a 1N solution of HCl in anhydrous ethyl ether. After agitation for 30 minutes at 23° C., the solution is concentrated to dryness under vacuum. The solid which appears is taken up in 10 ml of dry ethyl ether and filtered through a Buichner, after washing twice with 10 ml of dry ethyl ether, the solid is removed and dried overnight in an oven at 60° C. In this way the hydrochloride is obtained in the form of a light beige powder with a yield of 69%. Melting point: 210–212° C.

NMR $^{13}$C (DMSO d6, 100 MHz, δ): 12.02; 12.23; 13.00; 14.63; 20.55; 24.80; 25.00; 30.98; 42.72; 50.80; 53.34; 77.44; 78.28; 87.85; 107.23; 113.66; 117.17; 120.83; 120.85; 123.16; 139.76; 143.60; 145.21; 146.35; 153.80; 171.15.

MS (%): 463.2 (M+1, 100).

IR: $\nu_{C=O}$ (amide): 1670 cm$^{-1}$.

Example 5

1-[4-(2-amino-5-pyridinyl)butyl]-4-[(3,4-dihydro-6-hydroxy-2,5,7,8-tetramethyl-2H-[1]-benzopyran-2-yl)carbonyl]-piperazine hydrochloride: 5

In a stainless steel autoclave, 0.15 g (0.32 mmole) of compound 4.2 (free base) is dissolved in 10 ml of ethanol in the presence of 0.1 g of Pd/C at 10%. The reaction mixture is agitated under a hydrogen atmosphere (1.5 bar) for 1 hour and a half at 23° C.

The catalyst is then eliminated by filtration and the ethanolic solution is concentrated under vacuum. The residue is purified on a silica column (eluant: dichloromethane/ethanol: 5/1). In this way the free base is obtained in the form of a white powder with a yield of 54%. The product is salified under the conditions described previously. White powder. Melting point: 221–223° C.

NMR $^{13}$C (DMSO d6, 100 MHz, δ): 12.04; 12.25; 13.04; 20.58; 22.28; 23.83; 25.12; 27.01; 29.84; 30.64; 31.07; 42.67; 50.75; 51.02; 55.07; 78.30; 113.59; 117.18; 120.84; 120.88; 123.18; 125.48; 133.51; 143.63; 145.31; 146.35; 153.12; 171.14.

MS (%): 467.3 (M+1, 100).

IR: $\nu_{C=O}$ (amide): 1671 cm$^{-1}$.

Example 6

1-12-(6-amino-4-methyl-2-pyridinyl)ethyl]4-1(3,4-dihydro-6-hydroxy-2,5,7,8-tetramethyl-2H-[1-benzopyran-2-yl)carbonyl]-piperazine hydrochloride: 6

6.1) 6-(2,5-dimethylpyrrol-1-yl)-4-methyl-2-pyridineethanol:

A solution of 1 g (5 mmoles) of 2-(2,5-dimethylpyrrol-1-yl)-4,6-dimethylpyridine (prepared from 6-amino-2,4-lutidine according to *J. Chem. Soc. Perkin Trans.*, (1984), 12, 2801–2807) in 5 ml of anhydrous ethyl ether is added dropwise to a solution, cooled down to −20° C., of 2.47 ml (6.15 mmoles) of nBuLi (2.5M in hexane) in 10 ml of anhydrous ethyl ether. After agitation for one hour at between −20 and −15° C., the internal temperature is taken to 23° C. and agitation is maintained for half an hour at this temperature, during which period a precipitate appears. The reaction mixture is then diluted with 3.5 ml of anhydrous THF and its temperature lowered to −20° C. before the addition in one portion of 0.6 g of paraformaldehyde. The temperature of the medium is then taken to 23° C. and agitation is maintained for an additional half hour. Finally the reaction is neutralized by the addition of 20 ml of a saturated aqueous solution of $NH_4Cl$. After decanting, the aqueous phase is extracted twice with 30 ml of ethyl acetate. The organic phases are collected and washed twice with 20 ml of salt water. After drying over sodium sulphate, the organic solution is dried, filtered and concentrated under vacuum. The evaporation residue is purified on a silica gel column (eluant: heptane/ethyl acetate: 2/1). A colourless oil is obtained with a yield of 24%.

NMR 1H (CDCl$_3$, 400 MHz, δ): 1.27 (s, 1H, OH); 2.14 (s, 6H, 2 CH$_3$ pyrrole); 2.41 (s, 3H, CH$_3$); 3.03 (m, 2H, CH$_2$); 4.03 (m, 2H, CH$_2$—OH); 5.90 (s, 2H, pyrrole); 6.91 (s, 1H, pyridine); 7.01 (s, 1H, pyridine).

6.2) 6-(2,5-dimethylpyrrol-1-yl)-4-methyl-2-pyridineethanol p-toluenesulphonate:

A solution of 1.65 g (8.69 mmoles) of p-toluene sulphonyl chloride in 3 ml of dichloromethane is added to a mixture of 2 g (8.69 mmoles) of intermediate 6.1 and 0.87 g (8.69 mmoles) of triethylamine in solution in 15 ml of dichloromethane, cooled down using an ice bath. The reaction mixture is agitated at 23° C. for 16 hours, concentrated under vacuum and the residue is diluted with 40 ml of ethyl acetate. After washing 3 times with 20 ml of water followed by 20 ml of salt water, the organic solution is dried over sodium sulphate, filtered and concentrated under vacuum. The residue is purified on a silica column (eluant: heptane/ethyl acetate: 4/1). A beige powder is obtained with a yield of 71%.

NMR $^1$H (CDCl$_3$, 100 MHz, δ): 2.10 (s, 6H, 2 CH$_3$ pyrrole); 2.39 (s, 3H, CH$_3$); 2.42 (s, 3H, CH$_3$); 3.14 (m, 2H, CH$_2$); 4.40 (m, 2H, CH$_2$—O); 5.78 (s, 2H, pyrrole); 6.91 (s, 1H, pyridine); 7.00 (s, 1H, pyridine); 7.56 (m, 4H, Ph).

6.3) 1-[(dimethylethoxy)carbonyl]-4-{2-[6-(2,5-dimethylpyrrol-1-yl)-4-methyl-2-pyridinyl]ethyl}piperazine:

2.15 g (5.6 mmoles) of intermediate 6.2, 0.73 g (3.9 mmoles) of N-Boc-piperazine, 3.65 g (11.2 mmoles) of caesium carbonate and 0.037 g (0.28 mmole) of LiI are dissolved successively in 10 ml of butanone. The mixture is heated under reflux for 16 hours. After returning to 23° C., 50 ml of water and 50 ml of ethyl acetate are added. The organic phase is decanted, washed twice with 20 ml of water and with 20 ml of salt water, dried over sodium sulphate, filtered and concentrated under vacuum. The residue is purified on a silica column (eluant: heptane/ethyl acetate: 1/1). A dark yellow oil is obtained with a yield of 65%.

NMR 1H (CDCl$_3$, 100 MHz, δ): 1.44 (s, 9H, tBu); 2.12 (s, 6H, 2 CH$_3$ pyrrole); 2.41 (s, 3H, CH$_3$); 2.44 (m, 4H, 2 CH$_2$); 2.90 (m, 4H, 2 CH$_2$); 3.41 (m, 4H, 2 CH$_2$); 5.86 (s, 2H, pyrrole); 6.91 (s, 1H, pyridine); 7.00 (s, 1H, pyridine).

6.4) 1-{2-[6-(2,5-dimethylpyrrol-1-yl)-4-methyl-2-pyridinyl]ethyl}piperazine: 100 ml of a 6N aqueous solution of HCl is added dropwise to a solution of 5.3 g (16.5 mmoles) of intermediate 6.3 in 150 ml ethyl acetate. After agitation for one hour at 23° C., the reaction mixture is decanted. The aqueous phase is collected, rendered basic (pH=11) by the addition of a 2N aqueous solution of soda and the product is finally extracted twice with 100 ml of dichloromethane. The organic phases are collected and washed twice with 50 ml of salt water. After decanting, the organic solution is dried over sodium sulphate, filtered and concentrated under vacuum. An orange oil is obtained with a yield of 87%.

NMR 1H (CDCl$_3$, 100 MHz, δ): 2.12 (s, 6H, 2 CH$_3$ pyrrole); 2.40 (s, 3H, CH$_{3)}$, 2.50 (m, 4H, 2 CH$_2$); 2.86 (m, 8H, 4 CH$_2$); 5.84 (s, 2H, pyrrole); 6.84 (s, 1H, pyridine); 7.00 (s, 1H, pyridine).

6.5) 1-[(3,4-dihydro-6-hydroxy-2,5,7,8-tetramethyl-2H-[1]-benzopyran-2-yl)carbonyl]-4-[{2-[6-(2,5-dimethylpyrrol-1-yl)-4-methyl-2-pyridinyl]ethyl}piperazine:

1.65 g (10.2 mmoles) of 1,1'-carbonyldiimidazole is added to a solution of 2.5 g (10 mmoles) of 3,4-dihydro-6-hydroxy-2,5,7,8-tetramethyl-2H-[1]-benzopyran-2-carboxylic acid (Trolox) in 20 ml of THF. After agitation for one hour at 23° C., a solution of 2.2 g (10 mmoles) of intermediate 6.4 in 10 ml of THF is added dropwise over 10 minutes. The reaction mixture is agitated at 23° C. for 16 hours and finally concentrated under vacuum. The residue is then dissolved in 100 ml of a mixture of dichloromethane/water (2/1). After decanting, the organic solution is successively washed with twice 20 ml of water, with 20 ml of salt water, dried over sodium sulphate, filtered and finally concentrated under vacuum. The evaporation residue is purified on a silica column (eluant: heptane/ethyl acetate: 1/5). A white powder is obtained with a yield of 70%. Melting point: 82–84° C.

NMR $^1$H (CDCl$_3$, 100 MHz, δ): 1.58–3.04 (m, 30H, Trolox+2 CH$_3$ pyrrole +4 CH$_2$), 3.60 (m, 2H, CH$_2$), 4.00 (m, 2H, CH$_2$), 5.88 (s, 2H, pyrrole), 6.84 (s, 1H, pyridine), 6.98 (s, 1H, pyridine).

6.6) 1-[2-(6-amino-4-methyl-2-pyridinyl)ethyl]-4-[(3,4-dihydro-6-hydroxy-2,5,7,8-tetramethyl-2H-[1]-benzopyran-2-yl)carbonyl]-piperazine hydrochloride:

The experimental protocol used is the same as that described for intermediate 1.6, intermediate 6.5 replacing intermediate 1.5. The expected product is obtained in the form of a white powder with a yield of 40% after salification. Melting point: 179–182° C.

NMR $^1$H (pyridine d5, 400 MHz, δ): 0.97–1.93 (m, 16H, Trolox, 1.35 (s, 3H, CH$_3$ pyridine), 2.10 (m, 3H, CH$_2$+½ CH$_2$), 2.30 (m, 2H, CH$_2$), 2.40 (m, 3H, CH$_2$+½ CH$_2$), 2.95 (broad s, 1H, ½ CH$_2$), 3.19 (broad s, 1H, ½ CH$_2$), 3.59 (broad s, 2H, CH$_2$), 5.67 (s, 1H, pyridine), 5.85 (s, 1H, pyridine). IR: $v_{C=O}$ (amide): 1662 cm$^{-1}$.

Example 7

1-[4-(2-amino-6-pyridinyl)-3-butynyl]4-[(3,4-dihydro-6-hydroxy-2,5,7,8-tetramethyl-2H-[1]-benzopyran-2-yl)carbonyl]-piperazine hydrochloride: 7

The experimental protocol used is the same as that described for intermediate 4,2,2-amino-6-bromo-pyridine replacing 2-amino-5-bromo-pyridine. The expected product is obtained in the form of a pale yellow powder. Melting point: 172–175° C.

NMR 1H (DMSO d6, 400 MHz, δ): 1.50 (s, 3H, $CH_3$); 1.95 (s, 3H, $CH_3$); 2.00 (m, 2H, $ΩCH_2$—$CH_2$); 2.05 (s, 6H, 2×$CH_3$); 2.55 (m, 2H, $ΩCH_2$—$CH_2$); 3.15 (m, 4H, $CH_2N$); 3.35 (m, 4H, $CH_2N$); 3.50 (m, 4H, $CH_2$—$CH_2$—C ... C—); 6.80 (m, 2H, pyridine); 7.55 (broad s, 1H, $NH^+$); 7.80 (m, 1H, pyridine); 8.00 (broad s, 1H, $NH^+$).

IR: $v_{C=O}$ (amide): 1656 $cm^{-1}$.

Example 8

N-1(6-amino-4-methyl-2-pyridinyl)butyl]-2-hydroxy-5-methoxy-benzamide hydrochloride: 8

8.1) 6-(2,5-dimethyl-1H-pyrrol-1-yl)-4-methyl-2-pyrdine-butanamine:

The experimental protocol used is the same as that described for intermediate 1,1,1-(3-bromopropyl)-2,2,5,5-tetramethyl-1-aza-2,5-disilacyclopentane replacing the trimethyl 4-bromobutyrate. A yellow oil is obtained with a yield of 62%.

NMR $^1$H (CDCl$_3$, 400 MHz, δ): 1.52 (m, 2H, $CH_2$); 1.78 (m, 2H, $CH_2$); 2.11 (s, 6H, 2×$CH_3$ pyrrole); 2.39 (s, 3H, CH3 pyridine); 2.72 (t, 2H, $CH_2$, J=7.02 Hz); 2.79 (t, 2H, $CH_2$, J=7.62 Hz); 5.87 (s, 2H, pyrrole); 6.85 (s, 1H, pyridine); 6.98 (s, 1H, pyridine).

8.2) N-{4[6-(2,5-dimethyl-1H-pyrrol-1-yl)-4-methyl-2-pyridinyl]butyl}-2-hydroxy-5-methoxy: benzamide:

0.515 g (2 mmoles) of intermediate 8.1, 0.3 ml of triethylamine, 0.27 g (2 mmoles) of hydroxybenzotriazole and 0.38 3 g (2 mmoles) of 1-(3-dimethylaminopropyl)-3-ethyl-carbodiimide hydrochloride are added successively to a solution of 0.336 g (2 mmoles) of 2-hydroxy-5-methoxy-benzoic acid in 20 ml of dichloromethane. After having agitated the reaction mixture overnight at 25° C., the whole is diluted with 40 ml of water and agitation is maintained for another 10 minutes. The product is finally extracted with twice 50 ml of dichloromethane. The organic solution is dried over sodium sulphate, filtered and concentrated under vacuum. The evaporation residue is purified on a silica column (eluant ethyl acetate/heptane: 7/3) in order to produce a yellow oil with a yield of 47%.

NMR $^1$H (DMSO d6, 400 MHz, δ): 1.56 (m, 2H, $CH_2$); 1.71 (m, 2H, $CH_2$); 2.00 (s, 6H, 2×$CH_3$ pyrrole); 2.34 (s, 3H, CH, pyridine); 2.73 (m, 2H, $CH_2$); 3.30 (m, 2H, $CH_2$); 3.71 (s, 3H, $OCH_3$); 5.75 (s, 2H, pyrrole); 6.80–7.38 (m, 5H, arom.); 8.83 (broad t, 1H, CONH, J=5.44 Hz); 12.20 (broad s, 1H, arom. OH).

8.3) N-[(6-amino-4-methyl-2-pyridinyl)butyl]-2-hydroxy-5-methoxy-benzamide hydrochloride:

The experimental protocol used is the same as that described for compound 1.6, intermediate 8.2 replacing intermediate 1.5. A mauve coloured solid is obtained with a yield of 29%. Melting point: 131–134° C.

NMR 1H (DMSO d6, 400 MHz, δ): 1.55 (m, 2H, $CH_2$); 1.69 (m, 2H, $CH_2$); 2.27 (s, 3H, $CH_3$ pyridine); 2.69 (t, 2H, $CH_2$, J=7.4 Hz); 3.31 (m, 2H, $CH_2$); 3.73 (s, 3H, $OCH_3$); 6.59–7.45 (m, 5H, arom.); 7.74 (broad s, 2H, $NH_2$); 8.96 (t, 1H, CONH, J=5.36 Hz), 12.20 (broad s, 1H, $NH^+$); 13.93 (broad s, 1H, arom. OH).

IR: vc=o(amide): 1640–1660 $cm^{-1}$.

Example 9

N-[(6-amino-4-methyl-2-pyridinyl)butyl]-2,6-dihydroxy-benzamide: 9

The experimental protocol used is the same as that described for Example 8, 2,6-dihydroxy-benzoic acid replacing 2-hydroxy-5-methoxy-benzoic acid. The free base is obtained in the form of a pale pink solid with a yield of 41%. Melting point: 158–159° C.

NMR $^1$H (DMSO d6, 400 MHz, δ): 1.06–1.62 (m, 4H, 2×$CH_2$); 2.07 (s, 3H, $CH_3$ pyridine), 2.45 (m, 2H, $CH_2$); 3.34 (m, 2H, $CH_2$); 5.75 (broad s, 2H, $NH_2$); 5.73–6.40 )m, 5H, arom.); 7.13 (broad s, 1H, CONH); 9.00 (broad s, 1H, OH); 12.00 (broad s, 1H, OH).

Example 10

N-[(6-amino-4-methyl-2-pyridinyl)butyl]-2,5-dihydroxy-benzamide hydrochloride: 10

The experimental protocol used is the same as that described for Example 8, 2,5-dihydroxy-benzoic acid replacing 2-hydroxy-5-methoxy-benzoic acid. A white solid is obtained with a yield of 45%. Melting point: 105–106° C.

NMR $^1$H (DMSO d6, 400 MHz, δ): 1.54 (m, 2H, $CH_2$); 1.67 (m, 2H, $CH_2$); 2.27 (s, 3H, $CH_3$ pyridine); 2.69 (m, 2H, $CH_2$); 3.29 (m, 2H, $CH_2$); 6.59–7.24 (m, 5H, arom.); 7.73 (broad s, 2H, $NH_2$); 8.76 (t, 1H, CONH, J=5.16 Hz); 9.06 (broad s, 1H, $NH^+$); 11.80 (broad s, 1H, OH); 13.86 (broad s, 1H, OH).

IR: $v_{C=O}$ (amide): 1658 $cm^{-1}$.

Example 11

5-amino-N-[(6-amino-4-methyl-2-pyridinyl)butyl]-2-hydroxy-benzamide hydrochloride: 11

11.1) 5-[(1,1-dimethylethoxy)carbonyl]amino-N-{4-[6-(2,5-dimethyl-1H-pyrrol-1-yl)-4-methyl-2-pyridinyl]butyl}-2-hydroxy benzamide:

The experimental protocol used is the same as that described for intermediate 8,2,5-tert-butoxycarbonylamino-2-hydroxy benzoic acid (J. Med. Chem., (1994), 37 (6), 845–859) replacing 2-hydroxy-5-methoxy-benzoic acid. A white foam is obtained with a yield of 33%.

NMR $^1$H (DMSO d6, 400 MHz, δ): 1.45 (s, 9H, tBu); 1.54 (m, 2H, $CH_2$); 1.65 (m, 2H $CH_2$); 2.01 (s, 6H, 2×$CH_3$ pyrrole); 2.44 (s, 3H, $CH_3$ pyridine); 2.67 (m, 2H, $CH_2$); 3.29 (m, 2H, $CH_2$); 5.75 (s, 2H, pyrrole); 6.79–7.85 (m, 5H, arom.); 8.71 (t, 1H, CONH, J=5.48 Hz); 9.11 (broad s, 1H, NH-Boc); 11.89 (broad s, 1H, OH).

11.2) 5-amino-N-[(6-amino-4-methyl-2-pyridinyl)butyl]-2-hydroxy-benzamide hydrochloride:

The experimental protocol used is the same as that described for compound 1.6, intermediate 11.1 replacing intermediate 1.5. Detachment of tert-butyl carbamate is carried out in ethanol in the presence of a 3N aqueous solution of HCl. The hydrochloride is obtained in the form of a light beige solid with a yield of 15%. Melting point: decomposition at 180° C.

NMR $^1$H (DMSO d6, 400 MHz, δ): 1.58 (m, 4H, $CH_2$); 2.37 (s, 3H, $CH_3$ pyridine); 2.59 (m, 2H, $CH_2$); 3.34 (m, 2H, $CH_2$); 6.62 (s, 2H, pyridine); 7.08–7.85 (m, 3H, arom.); 7.76 (broad s, 2H, $NH_2$); 8.85 (t, 1H, CONH, J=5.48 Hz); 10.09 (broad s, 1H, $NH^+$); 10.29 (broad s, 2H, $NH_2$ aniline); 12.28 (broad s, 1H, OH).

IR: $v_{C=O}$ (amide): 1662 $cm^{-1}$.

Example 12

N-[(6-amino-4-methyl-2-pyridinyl)butyl]-2,5-dihydroxy-3-methyl-benzamide hydrochloride: 12

The experimental protocol used is the same as that described for Example 8, 2,5-dihydroxy-3-methyl benzoic acid (Can. *J. Chem.*, (1972), 50, 1276–82) replacing 2-hydroxy-5-methoxy-benzoic acid. A beige solid is obtained with a yield of 43%. Melting point: 189–190° C.

NMR $^1$H (DMSO d6, 400 MHz, δ): 1.53 (m, 2H, $CH_2$); 1.67 (m, 2H, $CH_2$); 2.07 (s, 3H, $CH_3$ phenol); 2.27 (s, 3H, $CH_3$ pyridine); 2.67 (m, 2H, $CH_2$); 3.26 (m, 2H, $CH_2$); 6.58–7.05 (m, 4H, arom.); 7.74 (broad s, 2H, $NH_2$); 8.80 (broad s, 1H, CONH); 8.93 (broad s, 1H, OH); 12.47 (s, 1H, OH); 13.90 (broad s, 1H, $NH^+$).

IR: $v_{C=O}$ (amide): 1630 $cm^{-1}$.

Example 13

N-1(6-amino-4-methyl-2-pyridinyl)butyl]-2,5-dihydroxy-3-(1-methylethyl)-benzamide: 13

The experimental protocol used is the same as that described for Example 8, 2,5-dihydroxy-3-isopropyl benzoic acid (prepared according to the method described in *Can. J. Chem.*, (1972), 50, 1276–82) replacing 2-hydroxy-5-methoxy-benzoic acid. A pale pink solid with a yield of 14%. Melting point: 164–165° C.

NMR $^1$H (DMSO d6, 400 MHz, δ): 1.13 (d, 6H, $CH_3$ (isopropyl), J=6.5 Hz); 1.52–1.60 (m, 4H, 2×$CH_2$); 2.08 (s, 3H, $CH_3$ pyridine); 2.44 (m, 2H, $CH_2$); 3.19 (m, 1H, CH); 3.26 (m, 2H, $CH_2$); 5.66 (s, 2H, $NH_2$); 6.05 (s, 1H, pyridine); 6.18 (s, 1H, pyridine); 6.82 (s, 1H, arom.); 7.04 (s, 1H, arom.); 8.74 (broad s, 1H, CONH); 8.88 (broad s, 1H, OH); 12.69 (broad s, 1H, OH).

Example 14

N-[(6-amino-4-methyl-2-pyridinyl)butyl]-2-hydroxy-4,6 dimethoxy-benzamide hydrochloride: 14

The experimental protocol used is the same as that described for Example 8, 2,4-dimethoxy-6-hydroxy benzoic acid replacing 2-hydroxy-5-methoxy-benzoic acid. A white solid is obtained with a yield of 27%. Melting point: 183–184° C.

NMR $^1$H (DMSO d6, 400 MHz, δ): 1.52 (m, 2H, $CH_2$); 1.65 (m, 2H, $CH_2$); 2.25 (s, 3H, $CH_3$ pyridine); 2.67 (m, 2H, CH $_2$); 3.31 (m, 2H, $CH_2$); 3.74 (s, 3H, $OCH_3$); 3.86 (s, 3H, $OCH_3$); 6.05 (s, 1H, pyridine); 6.10 (s, 1H, pyridine); 7.60 (m, 2H, arom.); 7.76 (broad s, 2H, $NH_2$); 8.57 (broad t, 1H, CONH, J=5.37 Hz); 14.02 (broad s, 1H, $NH^+$); 14.40 (s, 1H, OH).

IR: $v_{C=O}$ (amide): 1661 $cm^{-1}$.

Example 15

N-[(6-amino-4-methyl-2-pyridinyl)butyl]-3,5-bis-(1,1-dimethylethyl)-4-hydroxy-benzamide hydrochloride: 15

The experimental protocol used is the same as that described for Example 8, 3,5-di-tert-butyl-4-hydroxy-benzoic acid replacing 2-hydroxy-5-methoxy-benzoic acid. A white solid is obtained with a yield of 53%. Melting point: 259–260° C.

NMR $^1$H (DMSO d6, 400 MHz, δ): 1.38 (s, 18H, 2×tBu); 1.55 (m, 4H, 2×$CH_2$); 2.36 (s, 3H, $CH_3$ pyridine); 2.57 (m, 2H, $CH_2$); 3.23 (m, 2H, $CH_2$); 6.60 (s, 2H, pyridine); 7.39 (s, 1H, NH+); 7.56 (s, 2H, arom.); 7.73 (broad s, 2H, $NH_2$); 8.31 (t, 1H, CONH, J=5.6 Hz); 13.91 (s, 1H, OH).

IR: $v_{C=O}$ (amide): 1662 $cm^{-1}$.

Example 16

6-amino-N-[3,5-bis(1,1-dimethylethyl)-4-hydroxyphenyl]-4-methyl-2-pyridineheptanamide hydrochloride: 16

16.1) 6-(2,5-dimethyl-1H-pyrrol-1-yl)-4-methyl-2-pyridineheptanol:

The experimental protocol used is the same as that described for intermediate 2.1, the trimethylsilylated derivative of 6-bromo-1-hexanol (*J Org. Chem.*, (1988), 53 (12), 2732–7) replacing the 2-(3-chloropropoxy)tetrahydro-2H-pyrane. The crude product obtained is then dissolved in THF and treated with a solution (1M in THF) of tetrabutylammonium fluoride (1.2–1.5 eq.) at 20° C. After agitation for one hour, a saturated solution of ammonium chloride is added dropwise. The mixture is finally concentrated under vacuum and the residue is taken up in dichloromethane. The organic phase is washed with water followed by salt water, dried over sodium sulphate, filtered and concentrated under vacuum. The residue is purified on a silica gel column (eluant dichloromethane/methanol: 98/2). A clear yellow oil is obtained with a yield of 79%.

16.2) 6-amino-N-[3,5-bis(1,1-dimethylethyl)-4-hydroxyphenyl]-4-methyl-2-pyridineheptanamide hydrochloride:

The experimental protocol used is the same as that described for the successive intermediates 2.3 to 2.6, starting from the alcoholic derivative 16.1 instead of intermediate 2.2. White powder. Melting point: 149–151° C.

NMR $^1$H (DMSO d6, 400 MHz, δ): 1.20–1.45 (m, 22H, 2×tBu +2×$CH_2$); 1.56 (broad s, 2H, $CH_2$); 1.64 (broad s, 2H, $CH_2$); 2.23 (t, 2H, $CH_2$); 2.27 (s, 3H, $CH_3$ pyridine); 2.63 (t, 2H, $CH_2$); 6.57 (s, 1H, pyridine); 6.59 (s, 1H); 7.39 (s, 2H, arom.); 7.72 (broad s, 2H, $NH_2$); 9.59 (s, 1H); 13.78 (s, 1H, $NH^+$).

IR: $v_{C=O}$ (amide): 1656 $cm^{-1}$.

Example 17

6-amino-N-[3,5-bis(1,1-dimethylethyl)-4-hydroxyphenyl]-4-methyl-2-pyridinehexanamide hydrochloride: 17

The experimental protocol used is the same as that described for compound 16, the trimethylsilylated derivative of 5-chloro-1-pentanol (prepared according to *J. Org. Chem.*, (1988), 53 (12), 2732–7) replacing the trimethylsilyl derivative of 6-bromo-1-hexanol. Off-white solid. Melting point: 101–103° C.

NMR $^1$H (DMSO d6, 400 MHz, δ): 1.34 (m, 20H, 2×tBu+$CH_2$); 1.57 (m, 2H, $CH_2$); 1.65 (m, 2H, $CH_2$); 2.25 (m, 5H, $CH_2$+$CH_3$ pyridine); 2.65 (t, 2H, $CH_2$); 6.59 (s, 2H, pyridine+OH); 6.72 (s, 1H, pyridine); 7.39 (s, 2H, arom.); 7.74 (broad s, 2H, $NH_2$); 9.61 (s, 1H, CO—NH); 13.82 (s, 1H, $NH^+$).

IR: $v_{C=O}$ (amide): 1661 $cm^{-1}$.

Example 18

6-amino-N-[3,5-bis(1,1-dimethylethyl)-4-hydroxyphenyl]-4-methyl-2-pyridineacetamide hydrochloride: 18

18.1) 6-(2,5-dimethyl-1H-pyrrol-1-yl)-4-methyl-2-pyridine acetic acid:

The experimental protocol used is the same as that described for intermediate 2.1, carbon dioxide replacing 2-(3-chloropropoxy)tetrahydro-2H-pyrane. The crude reaction product is purified on a silica column (eluant:

dichloromethane/ethanol: 95/5). A pale yellow oil is obtained with a yield of 45%.

NMR $^1$H (CDCl$_3$, 400 MHz, δ): 2.15 (s, 6H, 2×CH$_3$); 2.50 (s, 3H, CH$_3$); 3.90 (s, 2H, CH$_2$); 5.90 (s, 2H, pyrrole); 7.00 (s, 1H, pyridine); 7.10 (s, 1H, pyridine); 8.0–9.0 (hump, CO$_2$H).

18.2) 6-amino-N-[3,5-bis(1,1-dimethylethyl)-4-hydroxyphenyl]-4-methyl-2-pyridineacetamide hydrochloride:

The experimental protocol used is the same as that described for intermediates 1.5 and 1.6. Solid with an off-white colour. Melting point: 258–260° C.

NMR $^1$H (DMSO d6, 400 MHz, δ): 1.50 (s, 18H, 2×tBu); 2.45 (s, 3H, CH$_3$ pyridine); 3.95 (s, 2H, CH$_2$); 6.80 (d, 2H, pyridine); 6.95 (s, 1H, CO—NH); 7.55 (s, 2H, arom.); 8.00 (broad s, 1H, OH); 10.40 (s, 1H, NH$^+$).

Example 19

α-amino-N-[4-(dimethylamino)phenyl]-5-(6-amino-2-pyridinyl)-4-pentynamide hydrochloride: 19

19.1) N-(4-dimethylaminophenyl)-α-[(1,1-dimethylethoxycarbonyl)amino]-4-pentynamide:

0.73 ml (5.26 mmoles) of triethylamine, 0.71 g (5.26 mmoles) of hydroxy-benzotriazole, 1.02 g (4.78 mmoles) of 2-tert-butoxycarbonylamino-pent-4-ynoic acid and 2.014 g (10.52 mmoles) of 1(3-dimethylaminopropyl)-3-ethyl carbodiimide hydrochloride are added to a suspension of 1 g (4.78 mmoles) of N,N dimethyl-1,4-phenylenediamine dihydrochloride in 25 ml of dichloromethane. The reaction mixture is agitated for 16 hours at 23° C. and finally diluted with 50 ml of water. The organic phase is decanted and washed with 3×50 ml of water followed by 50 ml of salt water. After drying over sodium sulphate, the organic solution is filtered and concentrated under vacuum. The evaporation residue is purified on a silica column (eluant: dichloromethane/ethanol: 30/0.5). A beige solid is obtained with a yield of 56% (0.88 g).

NMR $^1$H (CDCl$_3$, 100 MHz, δ): 1.40 (s, 9H, tBu); 2.10 (m, 1H, CH); 2.75 (m, 2H, CH$_2$); 2.90 (s, 6H, 2×CH$_3$N); 4.40 (m, 1H, CH—CO); 5.45 (broad d, 1H, NH); 6.70 (m, 2H, arom.); 7.30 (m, 2H, arom.); 8.10 (broad s, 1H, NH).

19.2) 5-(6-amino-2-pyridinyl)-N-(4-dimethylaminophenyl)-α-[(1,1-dimethylethoxycarbonyl)amino]-4-pentynamide:

Intermediate 19.2 is prepared by condensation of intermediate 19.1 with 2-amino-6-bromo-pyridine under experimental conditions identical to those described for the synthesis of intermediate 4.2. A beige solid is obtained with a yield of 35% (0.4 g). Melting point: 192–194° C.

NMR $^1$H (CDCl$_3$, 100 MHz, δ): 1.45 (s, 9H, tBu); 2.90 (s, 6H, 2×CH$_3$N); 3.00 (m, 2H, CH$_2$—C . . . C—); 4.50 (m, 3H, NH$_2$+CH—CO); 5.50 (broad d, 1H, NH); 6.45 (d, 1H arom.); 6.70 (m, 3H arom.); 7.40 (m, 3H arom.); 8.10 (broad s, 1H, NH).

19.3) α-amino-N-[4-(dimethylamino)phenyl]-5-(6-amino-2-pyridinyl)-4-pentynamide hydrochloride:

5 ml of a 3N aqueous solution of hydrochloric acid is added to a solution, cooled down using an ice bath, of 0.4 g (0.94 mmole) of intermediate 19.2 in a mixture of 15 ml of ethanol and 5 ml of dichloromethane. After agitation for 5 minutes, the reaction medium is concentrated under vacuum. The evaporation residue is taken up in 25 ml of water and the aqueous phase is washed successively with 20 ml of heptane and with 20 ml of dichloromethane. After decanting, the aqueous solution is lyophilized in order to produce 0.13 g (30%) of a beige solid. Melting point$_{22}$ 250° C.

NMR $^1$H (DMSO d6, 400 MHz, δ): 3.00 (s, 6H, 2×CH$_3$); 3.30 (m, 2H, CH$_2$—C . . . C—); 4.30 (m, 1H, CH—CO); 7.00 (m, 2H, arom.); 7.55 (m, 2H, arom.); 7.75 (m, 2H, arom.); 7.85 (m, 1H, arom.).

IR: ν$_{C=O}$ (amide): 1655 cm$^{-1}$.

Example 20

α,6-diamino-N-[4-(dimethylamino)phenyl]-2-pyridinylpentanamide hydrochloride: 20

20.1) 6-amino-α-[(1,1-dimethylethoxycarbonyl)amino]-N-[4-(dimethylamino)phenyl]-2-pyridinyl-pentanamide:

The experimental protocol used is the same as that described for compound 5 intermediate 19.2 replacing compound 4.2. A light beige powder is obtained with a yield of 94%. Melting point: 63–66° C.

NMR $^1$H (CDCl3, 100 MHz, δ): 1.50 (s, 9H, tBu); 1.90 (m, 4H, CH—CH$_2$—CH); 2.70 (m, 2H, CH$_2$—Arom.); 2.90 (s, 6H, 2×CH$_3$N); 4.20 (broad s, 1H, CH—CO); 4.60 (broad s, 2H, NH$_2$); 5.80 (broad s, 1H, NH); 6.40 (m, 2H, arom.); 6.70 (d, 2H, arom.); 7.40 (m, 3H, arom.); 8.10 (broad s, 1H, NH).

20.2) α,6-diamino-N-[4-(dimethylamino)phenyl]-2-pyridinepentanamide hydrochloride:

The experimental protocol used is the same as that described for intermediate 19.3, intermediate. 20.1 replacing intermediate 19.2. A very hygroscopic beige powder is obtained with a yield of 57% (0.66 g).

NMR $^1$H (DMSO d6, 400 MHz, δ): 1.85 (m, 4H, CH$_2$—CH); 2.75 (m, 2H, CH$_2$—Arom.); 3.10 (s, 6H, 2×CH$_3$N); 4.20 (broad s, 1H, CH—CO); 6.70 (d, 2H, arom.); 7.70 (broad s, 2H, NH$^+$); 7.80 (m, 3H, arom.+NH$^+$); 7.90 (broad s, 2H, NH$^+$); 8.50 (broad s, 3H, arom.); 11.45 (broad s, 1H, NH$^+$); 14.40 (broad s, 1H, NH$^+$).

IR: ν$_{C=O}$ (amide): 1659 cm$^{-1}$.

Example 21

6-amino-N-[4-(dimethylamino)phenyl]4-methyl-2-pyridinehexanamide hydrochloride: 21

The experimental protocol used is the same as that described for compound 17, N,N-dimethyl-p-phenylenediamine replacing the 2,6-di-t-butyl-4-aminophenol. Hygroscopic grey solid.

NMR $^1$H (CDD$_3$OD, 400 MHz, δ): 1.43 (m, 2H, CH$_2$); 1.72 (m, 4H, 2×CH$_2$); 2.18 (s, 3H, CH$_3$); 2.34 (t, 2H, CH$_2$); 2.55 (t, 2H, CH$_2$); 2.90 (s, 6H, 2×CH$_3$); 6.25 (s, 1H, pyridine); 6.36 (s, 1H, pyridine); 6.77 (d, 2H, arom.); 7:35 (d, 2H, arom.).

MS: MH+=341.2.

Example 22

6-amino-N-[4-(dimethylamino)phenyl]-4-methyl-2-pyridineheptanamide hydrochloride: 22

The experimental protocol used is the same as that described for compound 16, N,N-dimethyl-p-phenylenediamine replacing the 2,6-di-t-butyl-4-aminophenol. Hygroscopic yellowish solid.

NMR $^1$H (CD$_3$OD, 400 MHz, δ): 1.48 (broad s, 4H, 2×CH$_2$); 1.74 (m, 4H, 2×CH$_2$); 2.37 (s, 3H, CH$_3$); 2.44 (t, 2H, CH$_2$); 2.73 (t, 2H, CH$_2$); 3.30 (s, 6H, 2×CH$_3$); 6.64 (s, 1H, pyridine); 6.66 (s, 1H, pyridine); 7.64 (d, 2H, arom.); 7.84 (d, 2H, arom.).

MS: MH+=355.2.

Example 23

N-[(6-amino-4-methyl-2-pyridinyl)butyl]-1,3-benzodioxole-5-carboxamide hydrochloride: 23

The experimental protocol used is the same as that described for compound 8, piperonylic acid replacing 2-hydroxy-5-methoxy-benzoic acid. Beige solid. Melting point: 176–178° C.

NMR $^1$H (DMSO d6, 400 MHz, δ): 1.51 (m, 2H, CH$_2$); 1.62 (m, 2H, CH$_2$); 2.27 (s, 3H, CH$_3$ pyridine); 2.68 (m, 2H, CH$_2$); 3.26 (m, 2H, CH$_2$); 6.07 (s, 2H, CH$_2$); 6.58 (m, 1H, arom.); 6.60 (s, 1H, pyridine); 6.95 (d, 1H, arom.); 7.39 (s, 1H, pyridine); 7.45 (d, 1H, arom.); 7.73 (broad s, 2H, NH$_2$); 8.35 (t, 1H, CONH); 13.92 (broad s, 1H, NH+).

MS: MH+=328.2.

Example 24

6-amino-N-[4-(dimethylamino)phenyl]-4-methyl-2-pyridinepentananamide hydrochloride: 24

The experimental protocol used is the same as that described for compound 1, N,N-dimethyl-p-phenylenediamine replacing 2,6-di-t-butyl-4-aminophenol. Hygroscopic grey solid.

NMR $^1$H (CD$_3$OD, 400 MHz, δ): 1.72 (m, 4H, 2×CH$_2$); 2.18 (s, 3H, CH$_3$); 2.35 (t, 2H, CH$_2$); 2.56 (t, 2H, CH$_2$); 2.88 (s, 6H, 2×CH$_3$); 6.24 (s, 1H, pyridine); 6.35 (s, 1H, pyridine); 6.76 (d, 2H, arom.); 7.34 (d, 2H, arom.).

MS: MH+=327.2.

Example 25

{[4-(6-amino-4-methyl-2-pyridinyl)butyl]amino}-N-[(4-dimethylamino)phenyl]-acetamide hydrochloride: 25

25.1) 2-amino-N-[4-(dimethylamino)phenyl)]acetamide:

Intermediate 25.1 is obtained after detachment of the tert-butoxycarbonyl function (see T. W. Greene and P. G. M. Wuts, *Protective Groups in Organic Synthesis*, Second edition (Wiley-Interscience, 1991)) of N-[4-(dimethylamino)phenyl)]-2-[(1,1-dimethylethoxy-carbonyl)amino]-acetamide, itself prepared according to an experimental protocol described in *Synth. Commun.*, (1993), 23 (9), 1339–1349. White solid. Melting point: 166–168° C.

NMR $^1$H (CDCl$_3$, 100 MHz, δ): 1.60 (broad s, 2H, NH$_2$); 2.90 (s, 6H, 2×CH$_3$); 3.45 (s, 2H, CH$_2$); 6.70 (d, 2H, arom.); 7.45 (d, 2H, arom.); 9.10 (broad s, 1H, NH).

25.2) 2-(3,3-dimethoxypropyl)-6-(2,5-dimethyl-1H-pyrrol-1-yl)-4-methylpyridine:

The experimental protocol used is the same as that described for intermediate 1.1, bromoacetaldehyde dimethylacetal replacing trimethyl 4-bromobutyrate. A yellow oil is obtained with a yield of 72%.

NMR $^1$H (CDCl$_3$, 100 MHz, δ): 1.90 (m, 2H, CH$_2$—CH(OCH$_3$)$_2$); 2.10 (s, 6H, 2×CH$_3$ pyrrole); 2.40 (s, 3H, CH$_3$ pyridine); 2.80 (m, 2H, CH$_2$—Arom.); 3.30 (s, 6H, 2×CH$_3$—O); 4.40 (t, 1H, CH(OCH$_3$)$_2$); 5.80 (s, 2H, pyrrole); 6.90 (d, 2H, pyridine).

25.3) 6-(2,5-dimethyl-1H-pyrrol-1-yl)-4-methyl-2-pyridine propanol:

A solution of 0.3 g (10.4 mmoles) of intermediate 25.2 in a mixture of 20 ml of acetic acid and 10 ml of a 1N aqueous solution of HCl is agitated for 18 hours at 23° C. The reaction mixture is then concentrated under vacuum and the residue dissolved in 50 ml of water. The aqueous solution is adjusted to pH 9–10 by the addition of NaHCO$_3$ and it is extracted with 2×100 ml of ethyl acetate. The organic phases are collected and washed with 100 ml of water followed by 100 ml of salt water. After drying over sodium sulphate, filtration and concentration under vacuum, the residue is purified on a flash silica column (eluant: ethyl acetate/heptane: 1/3). 0.1 g of a colourless oil is obtained (40%).

NMR $^1$H (CDCl$_3$, 100 MHz, δ): 2.10 (s, 6H, 2×CH$_3$ pyrrole); 2.40 (s, 3H, CH$_3$ pyridine); 3.00 (m, 4H, CH$_2$—CH$_2$); 5.80 (s, 2H, pyrrole); 6.90 (d, 2H, pyridine); 9.80 (s, 1H, CHO).

25.4) {{4-[6-(2,5-dimethyl-1H-pyrrol-1-yl)-4-methyl-2-pyridinyl]butyl}amino}-N-[(4-dimethylamino)phenyl] acetamide:

1 g of an activated pulverulent 4Å molecular sieve and 0.6 g (2.79 mmoles) of sodium triacetoxybdrohydride are added to a solution of 0.33 g (1.69 mmole) of intermediate 25.1 in 20 mil of anhydrous dichloro-1,2-ethane. The reaction mixture is cooled down to −15° C. and 0.45 g (1.86 mmole) of aldehyde 25.3 dissolved in 10 ml of anhydrous dichloro-1,2 ethane is added dropwise. After agitation for 18 hours at 23° C., the mixture is diluted with 50 ml of a saturated aqueous solution of NH$_4$Cl, followed by agitation and decanting. The aqueous phase is again extracted with 2×50 ml of dichloromethane. Finally, all the organic phases are collected and washed with 100 ml of salt water. This organic solution is then dried over sodium sulphate, filtered and concentrated under vacuum. The evaporation residue is then purified on a silica column (eluant: dichloromethane/ethanol: 20/1). A colourless oil is obtained with a yield of 15% (0.12g).

NMR $^1$H (CDCl$_3$, 100 MHz, δ): 2.00 (m, 2H, CH$_2$—pyridine); 2.10 (s, 6H, 2×CH$_3$ pyrrole); 2.30 (s, 3H, CH$_3$ pyridine); 2.40 (broad s, 1H, NH); 2.80 (m, 4H, CH$_2$—CH$_2$—N); 2.90 (s, 6H, 2×CH$_3$—N); 3.35 (s, 2H, N—CH$_2$—C=O); 5.80 (s, 2H, pyrrole); 6.70 (d, 2H, arom.); 6.90 (d, 2H, pyridine); 7.40 (d, 2H, arom.); 9.10 (broad s, 1H, NHCO).

25.5) {[4-(6-amino-4-methyl-2-pyridinyl)butyl]amino}-N-[(4-dimethylamino)phenyl]-acetamide:

The experimental protocol used is the same as that described for compound 1.6, intermediate 25.4 replacing intermediate 1.5. After chromatography on silica gel (eluant dichloromethane/ethanoltammonium hydroxide (20%): 20/0.5/0.5), a white solid is obtained with a yield of 46%.

25.6) {[4-(6-amino-4-methyl-2-pyridinyl)butyl]amino}-N-[(4-dimethylamino)phenyl]-acetamide hydrochloride:

The experimental protocol used is the same as that described for intermediate 19.3, intermediate 25.5 replacing intermediate 19.2. A very hygroscopic beige powder is obtained with a yield of 65% (0.038 g).

NMR $^1$H (DMSO d6, 400 MHz, δ): 2.10 (m, 2H, —CH$_2$—CH$_2$—CH$_2$—); 2.30 (s, 3H, CH$_3$ pyridine); 2.80 (m, 2H, —CH$_2$—N); 3.15 (m, 2H, CH$_2$—arom.); 3.25 (s, 6H, 2×CH$_3$—N 4.10 (s, 2H, N—CH$_2$—C=O); 6.60 (d, 2H, pyridine); 7.55 (d, 2H, arom.); 7.65 (d, 2H, arom.).

MS: MH+=341.

Example 26

6-amino-N-[13-(4-hydroxy-3-metboxy-phenyl)-2-propenyl]4-methyl-2-pyridinebutanamine hydrochloride: 26

26.1) 6-(2,5-dimethyl-1H-pyrrol-1-yl)-N-[3-(4-hydroxy-3-methoxy-phenyl)-2-propenyl]-4-methyl-2-pyridine-butanamine:

0.27 g (1.5 mmole) of 4-hydroxy-3-methoxycinnamaldehyde and 2 g of an activated 3Å molecular sieve are added to a solution of 0.39 g (1.5 mmole) of intermediate 8.1 in 15 ml of methanol. The reaction mixture is agitated for 24 hours at 20° C. before the addition, at 0° C., of 0.06 g (1.65 mmole) of NaBH$_4$, agitation is maintained, at 20° C., for another 24 hours. Finally the excess hydride is destroyed by the addition of 5 ml of water and the mixture is filtered on frit. The filtrate is concentrated under vacuum. The evaporation residue is purified on a silica column (eluant: CH$_2$Cl$_2$/MeOH/NH$_4$OH at 20%: 95/4.5/0.5). A brown oil is obtained with a yield of 40%.

26.2) 6-amino-N-[3-(4-hydroxy-3-methoxy-phenyl)-2-propenyl]-4-methyl-2-pyridine-butanamine hydrochloride:

The experimental protocol used is the same as that described for intermediate 1.6, intermediate 26.1 replacing intermediate 1.5. Brown solid. Melting point: 60–62° C.

NMR $^1$H (DMSO d6, 400 MHz, δ): 1.65 (m, 2H, CH$_2$); 1.72 (m, 2H, CH$_2$); 2.28 (s, 3H, CH$_3$ pyridine); 2.69 (broad s, 2H, CH$_2$); 2.94 (broad s, 2H, CH$_2$); 3.66 (broad s, 2H, CH$_2$); 3.72 (s, 3H, CH$_3$—O); 6.10 (m, 1H, —CH═CH—CH$_2$); 6.67 (d, 1H, —CH═CH—CH$_2$); 6.82 (d, 1H, arom.); 6.88 (d, 1H, arom.); 7.00 (s, 1H, arom.); 7.73 (broad s, 2H, NH$_2$); 8.91 (broad s, 2H, NH+OH); 9.23 (s, 1H, NH$^+$).

MS: MH+=342.3.

Example 27

6-amino-N-[4-chloro-2-(phenylamino)phenyl]-4-methyl-2-pyridinepentanamide hydrochloride: 27

The experimental protocol used is the same as that described for intermediate 1.5, 4-chloro-2-(phenylamino)-phenylamine (*Justus Liebigs Ann. Chem.*, (1909), 322) replacing 2,6-di-t-butyl-4-aminophenol. Beige powder. Melting point: 176–178° C.

NMR $^1$H (DMSO d6, 400 MHz, δ): 1.70 (broad s, 4H, 2×CH$_2$); 2.26 (s, 3H, CH$_3$); 2.62 (t, 2H, CH$_2$); 2.95 (t, 2H, CH$_2$); 6.54 (s, 1H, pyridine); 6.60 (s, 1H, pyridine); 7.32 (s, 1H, arom.); 7.40–8.00 (m, 8H, arom.); 14.1 (broad s, 1H, NHCO).

IR: $v_{C=O}$ (amide): 1660 cm$^{-1}$.

Example 28

N-[(6-amino-4-methyl-2-pyridinyl)butyl]-1,3-benzodioxole-5 acetamide hydrochloride: 28

The experimental protocol used is the same as that described for compound 8, 3,4-(methylenedioxy)-phenylacetic acid replacing 2-hydroxy-5-methoxy-benzoic acid. Beige solid.,Melting point: 56–58° C.

NMR $^1$H (DMSO d6, 400 MHz, δ): 1.42 (m, 2H, CH$_2$); 1.62 (m, 2H, CH$_2$); 2.27 (s, 3H, CH$_3$); 2.61 (t, 2H, CH$_2$); 3.05 (m, 2H, CH$_2$); 3.30 (s, 2H, CH$_2$—CO); 5.95 (s, 2H, O—CH$_2$—O); 6.53 (s, 1H, pyridine); 6.60 (s, 1H, pyridine); 6.68 (d, 1H, arom.); 6.79 (s, 1H, arom.); 6.81: (d, 1H, arom.); 7.76 (broad s, 2H, NH,); 8.05 (t, 1H, NH—CO); 13.99 (s, 1H, NH$^+$).

MS: MH+=342.2.

Example 29

N-[4-(6-amino-4-methyl-2-pyridinyl)butyl]-N-(1,3-benzodioxole-5-ylmethyl)amine fumarate: 29

The experimental protocol used is the same as that described for compound 26, piperonal replacing 4-hydroxy-3-methoxycinnamaldehyde. Beige solid. Melting point: 224–226° C.

NMR $^1$H (DMSO d6, 400 MHz, δ): 1.58 (s, 4H, 2×CH$_2$); 2.09 (s, 3H, CH$_3$); 2.43 (t, 2H, CH$_2$); 2.76 (t, 2H, CH$_2$); 3.93 (s, 2H, CH$_2$—NH); 5.95 (broad s, 3H, NH$_2$+NH); 6.01 (s, 2H, O—CH$_2$—O); 6.10 (s, 1H, fumarate); 6.20 (s, 1H, fumarate); 6.50 (s, 2H, pyridine); 6.91 (s, 2H, arom.); 7.05 (s, 1H, arom.).

MS:MH+=314.

Example 30

N-[4-(6-amino-4-methyl-2-pyridinyl)butyl]-N-[(E)-3-phenyl-2-propenyl]amine fumarate: 30

The experimental protocol used is the same as that described for compound 26, trans-cinnamaldehyde replacing 4-hydroxy-3-methoxycinnamaldehyde. Cream-coloured solid. Melting point: 163–165° C.

NMR $^1$H (DMSO d6, 400 MHz, δ): 1.61 (broad s, 4H, 2×CH$_2$); 2.08 (s, 3H, CH$_3$); 2.45 (t, 2H, CH$_2$); 2.85 (t, 2H, CH$_2$); 3.63 (d, 2H, CH═CH—CH); 4.47 (broad s, 1H, NH); 5.87 (broad s, 2H, NH$_2$); 6.10 (s, 1H, fumarate); 6.21 (s, 1H, fumarate); 6.31 (m, 1H, CH═CH—CH$_2$); 6.50 (s, 2H, pyridine); 6.72 (d, 1H, CH═CH—CH$_2$); 7.20–7.50 (m, 5H, arom.).

MS: MH+=296.

Example 31

(E)-N-[4-(6-amino-4-methyl-2-pyridinyl)butyl]-3-(1,3-benzodioxole-5-yl)-2-propenamide fumarate: 31

The experimental protocol used is the same as that described for compound 8 3,4-methylenedioxycinnamic acid replacing 2-hydroxy-5-methoxy-benzoic acid. Cream-coloured solid. Melting point: 111 –113° C.

NMR $^1$H (DMSO d6, 400 MHz, δ): 1.45 (m, 2H, CH$_2$); 1.61 (m, 2H, CH$_2$); 2.12 (s, 3H, CH$_3$); 2.49 (m, 2H, CH$_2$); 3.18 (m, 2H, CH$_2$); 6.05 (s, 2H, O—CH$_2$—O); 6.16 (s, 1H, fumarate); 6.26 (s, 1H, fumarate); 6.44 (d, 1H, CH═CH—CO); 6.60 (s, 2H, pyr.); 6.93 (d, 1H, arom.); 7.05 (d, 1H, arom.); 7.11 (s, 1H, arom.); 7.31 (d, 1H, CH═CH—CO); 7.97 (t, 1H, NH—CO).

MS: MH+=354.

Example 32

2-({[4-(6-amino-4-methyl-2-pyridinyl)butyl]amino}methyl)-4-methoxyphenol: 32

The experimental protocol used is the same as that described for intermediate 26.1, 2-hydroxy-5-methoxybenzaldehyde replacing 4-hydroxy-3-methoxycinnamaldehyde. Ochre oil.

NMR $^1$H (DMSO d6, 400 MHz, δ): 1.62 (m, 2H, CH$_2$); 1.74 (m, 2H, CH$_2$); 2.21 (s, 3H, CH$_3$); 2.57 (t, 2H, CH$_2$, J=7.5 Hz); 2.72 (t, 2H, CH$_2$, J=6.85 Hz); 3.74 (s, 3H, O—CH$_3$); 3.96 (s, 2H, CH$_2$—NH); 4.00–5.00 (broad s, 3H, NH$_2$+NH); 6.20 (s, 1H, pyridine); 6.34 (s, 1H, pyridine); 6.60 (s, 1H, arom.); 6.75 (m, 2H, arom.).

MS : MH+=316.

Example 33

N-[2-(benzyloxy)-4,5-dimethoxybenzyl]-4-[6-(2,5-dimethyl-1H-pyrrol-1-yl)-4-methyl-2-pyridinyl]-1-butanamine: 33

The experimental protocol used is the same as that described for intermediate 26.1, 2-benzyloxy-4,5-dimethoxybenzaldehyde replacing 4-hydroxy-3-methoxycinnamaldehyde. Brown oil.

NMR $^1$H (DMSO d6, 400 MHz, δ): 1.45 (m, 2H, CH$_2$); 1.67 (m, 2H, CH$_2$); 2.01 (s, 6H, 2×CH$_3$ (pyrrole)); 2.34 (s, 3H, CH$_3$); 2.50 (m, 2H, CH$_2$); 2.66 (m, 2H, CH$_2$); 3.64 (s, 2H, CH$_2$—NH); 3.66 (s, 3H, O—CH$_3$); 3.74 (s, 3H, O—CH$_3$); 4.40 (broad s, 1H, NH); 5.07 (s, 2H, O—CH$_2$—Ph); 5.75 (s, 2H, pyridine); 6.70–7.50 (m, 9H, arom.+pyridine).

Example 34

6-(4-{[2-(benzyloxy)-4,5-dimethoxybenzyl]amino}butyl)-4-methyl-2-pyridinamine: 34

The experimental protocol used is the same as that described for intermediate 1.6, compound 33 replacing intermediate 1.5. The free base is obtained as a brown foam.

NMR ¹H (CDCl₃, 400 MHz, δ): 1.66 (m, 2H, CH₂); 1.80 (m, 2H, CH₂); 2.18 (s, 3H, CH₃); 2.43 (m, 2H, CH₂); 2.86 (m, 2H, CH₂); 3.82 (s, 3H, O—CH₃); 3.86 (s, 3H, O—CH₃); 4.14 (s, 2H, CH₂—NH); 5.05 (s, 2H, O—CH₂—Ph); 5.20–6.10 (m, 3H, NH₂+NH); 6.20–7.40 (m, 9H, arom.+pyridine).

MS: MH+=436.

Example 35

2-({[4-(6-amino-4-methyl-2-pyridinyl)butyl]amino}methyl)-4,5-dimethoxyphenol : 35

This compound is obtained by debenzylation of compound 34 in the presence of hydrogen and Pd/C under standard conditions. Beige foam.

NMR ¹H (DMSO d6, 400 MHz, δ): 1.67 (m, 4H, 2×CH₂); 2.22 (s, 3H, CH₃); 2.60 (m, 2H, CH₂); 2.86 (m, 2H, CH₂); 3.68 (s, 3H, O—CH₃); 3.70 (s, 3H, O—CH₃); 3.97 (s, 2H, CH₂—NH); 6.50–7.00 (m, 4H, arom.+pyridine); 7.21 (broad s, 1H, OH); 9.10 (broad s, 2H, NH₂); 14.00 (broad s, 1H, NH).

MS: MH+=346.

Example 36

N-[4-(6-amino-4-methyl-2-pyridinyl)butyl]-6-hydroxy-2,5,7,8-tetramethyl-2-chromanecarboxamide fumarate: 36

The experimental protocol used is the same as that described for compound 8, 3,4-dihydro-6-hydroxy-2,5,7,8-tetramethyl-2H-[1]-benzopyran-2-carboxylic acid (Trolox) replacing 2-hydroxy-5-methoxy-benzoic acid. White solid. Melting point: 131–136° C.

NMR ¹H (DMSO d6, 400 MHz, δ): 1.30–1.35 (m, 2H, CH₂); 1.32 (s, 3H, Trolox); 1.42 (m, 2H, CH₂); 1.70 (m, 1H, CH₂ Trolox); 1.90–2.10 (4×s, 12H, 3×CH₃ Trolox+CH₃ Pyr.); 2.15 (m, 1H, CH₂ Trolox); 2.36 (m, 2H, CH₂); 2.50 (m, 2H, CH₂ Trolox); 3.08 (m, 2H, CH₂); 6.08 (broad s, 2H, NH₂); 6.11 (s, 1H, pyridine); 6.16 (s, 1H, pyridine); 6.58 (s, 1H, OH); 7.25 (broad t, 1H, NHCO, J=5.2 Hz).

MS: MH+=412.

Pharmacological Study of the Products of the Invention

Study of the Effects on Neuronal Constitutive NO Synthase of a Rat's Cerebellum

The inhibitory activity of the products of the invention is determined by measuring their effects on the conversion by NO synthase of [³H]L-arginine to [³H]L-citrulline according to the modified method of Bredt and Snyder (*Proc. Natl. Acad. Sci. USA*, (1990) 87: 682–685). The cerebellums of Sprague-Dawley rats (300g —Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 μl of incubation buffer containing 100 mM of HEPES (pH 7.4), 2 mM of EDTA, 2.5 mM of CaCl₂, 2 mM of dithiotreitol, 2 mM of reduced NADPH and 10 μg/ml of calmodulin are distributed. 25 μl of a solution containing 100 nM of [³H]L-arginine (Specific activity: 56.4 Ci/mmole, Amersham) and 40 μM of non-radioactive L-arginine is added. The reaction is initiated by adding 50 μl of homogenate, the final volume being 200 μl (the missing 25 μl are either water or the tested product). After 15 min, the reaction is stopped with 2 ml of stopping buffer (20 mM of HEPES, pH 5.5, 2 mM of EDTA). After passing the samples through a 1 ml column of DOWEX resin, the radioactivity is quantified by a liquid scintillation spectrometer. The compounds of Examples 1, 3, 8, 10, 12, 13, 21, 23 to 26, 29 to 32, 34 and 35 described above show an IC₅₀ lower than 5 μM.

Study of the Effects on Lipidic Peroxidation of the Cerebral Cortex of a Rat

The inhibitory activity of the products of the invention is determined by measuring their effects on the degree of lipidic peroxidation, determined by the concentration of malondialdehyde (MDA). The MDA produced by peroxidation of unsaturated fatty acids is a good indication of lipidic peroxidation (H Esterbauer and K H Cheeseman, Meth. Enzymol. (1990) 186: 407–421). Male Sprague Dawley rats weighing 200 to 250 g (Charles River) were sacrificed by decapitation. The cerebral cortex is removed, then homogenized using a Thomas potter in a 20 mM Tris-HCl buffer, pH=7.4. The homogenate is centrifuged twice at 50000 g for 10 minutes at 4° C. The pellet is kept at −80° C. On the day of the experiment, the pellet is replaced in suspension at a concentration of 1 g/15 ml and centrifuged at 515 g for 10 minutes at 4° C. The supernatant is used immediately to determine the lipidic peroxidation. The homogenate of rat's cerebral cortex (500 μl) is incubated at 37° C. for 15 minutes in the presence of the compounds to be tested or of solvent (10 μl). The lipidic peroxidation reaction is initiated by adding 50 μl of FeCl₂ at 1 mM, EDTA at 1 mM and ascorbic acid at 4 mM. After incubation for 30 minutes at 37° C., the reaction is stopped by adding 50 μl of a solution of hydroxylated di tertio butyl toluene (BHT, 0.2%). The MDA is quantified using a colorimetric test, by reacting a chromogenic reagent (R), N-methyl-2-phenylindol (650 μl) with 200 μl of the homogenate for 1 hour at 45° C. The condensation of an MDA molecule with two molecules of reagent R produces a stable chromophore the maximum absorbence wavelength of which is equal to 586 mn. (Caldwell et al. *European J. Pharmacol.* (1995) 285, 203–206). The compounds of Examples 1, 6, 13, 21, 24, 26 and 35 described above all show an IC₅₀ lower than 30 μM.

What is claimed is:

1. A compound of the formula

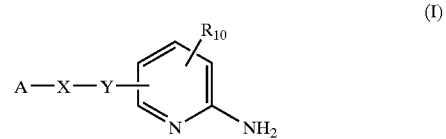

(I)

wherein A is selected from the group consisting of

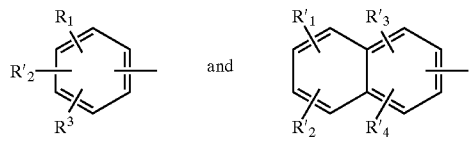

and

R₁, R₂ and R₃ are individually selected from the group consisting of hydrogen, halogen, —OH, —SH, alkyl and alkoxy of 1 to 6 carbon atoms, aralkoxy of 1 to 6 alkyl atoms, —O—CO—R₄, —SR₄—, —S(O)R₄, —SO$_2$R$_4$ and 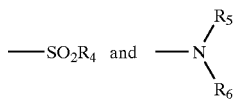

or R$_1$ and or R$_2$ or R$_2$ and R$_3$ together form methylenedioxy, R$_4$ is alkyl of 1 to 6 carbon atoms, R$_5$ and R$_6$ are individually selected from the group consisting of hydrogen, alkyl of 1 to 6 carbon atoms and aryl unsubstituted or substituted with at least one member of the group consisting of halogen, —OH and alkyl and alkoxy of 1 to 6 carbon atoms or taken together with the nitrogen atom form a heterocycle of 4 to 6 ring members containing 1 or 2 heteroatoms selected from the group consisting of oxygen, sulfur and =NR$_7$, R$_7$ is hydrogen or alkyl of 1 to 6 carbon atoms, R'$_1$, R'$_2$, R'$_3$ and R'$_4$ are individually selected from the group consisting of hydrogen, halogen, —OH and alkoxy of 1 to 6 carbon atoms, X is selected from the group consisting of

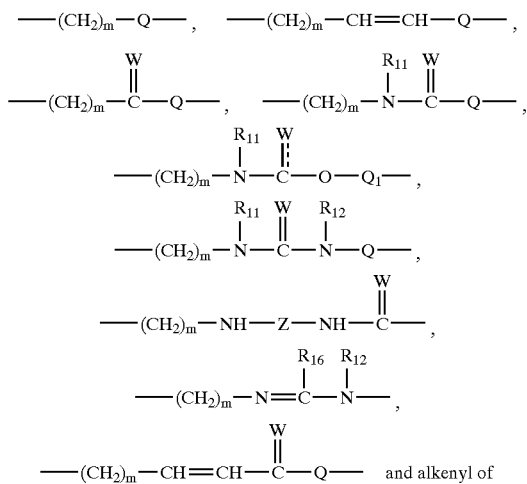

R'$_1$, R'$_2$, R'$_3$ and R'$_4$ are individually selected from the group consisting of hydrogen, halogen, —OH and alkoxy of 1 to 6 carbon atoms, R$_8$ is selected from the group consisting of hydrogen, alkyl of 1 to 6 carbon atoms, —COR$_9$ and aralkyl unsubstituted or substituted with at least one alkyl or alkoxy of 1 to 6 carbon atoms, X is selected from the group consisting of up to 6 carbon atoms, Q is selected from the group consisting of a bond, piperazine, homopiperazine, piperidine, pyrrolidine and azetidine, all unsubstituted or substituted with at least one alkyl of 1 to 6 carbon atoms, W is selected from the group consisting of oxygen, sulfur and =NH, Z is phenylene unsubstituted or substituted with at least one halogen, mn is an integer from 0 to 6, Y is selected from the group consisting of a) alkyl, alkenyl and alkynyl of up to 10 carbon atoms, each unsubstituted or substituted with

and b) —(CH$_2$)$_n$—O—(CH$_2$)$_p$—, —(CH$_2$)$_n$—S—(CH$_2$)$_p$— and —(CH$_2$)$_n$—NR$_{13}$—(CH$_2$)$_p$—, n and p are individually integers from 0 to 6, R$_{10}$ is selected from the group consisting of —OH, —CN, —NO$_2$, —SR$_{15}$ and alkyl and alkoxy of 1 to 6 carbon atoms, R$_{11}$, R$_{12}$, R$_{13}$, R$_{14}$ and R$_{15}$ are individually hydrogen or alkyl of 1 to 6 carbon atoms, R$_{16}$ is selected from the group consisting of hydrogen and alkyl and thio-allkyl of 1 to 6 carbon atoms with the proviso (1) that —X—Y— together are not a member of the group consisting of a single bond, alkylene, —O—, —S—, —NH— and —NH—CO—NH—alkylene, (2) when A is phenylene, —X—Y— together are not —NH—CO—NH— and (3) when A is 3,4,5-trialkoxy phenylene, —X—Y— together are not —CO—NH—CH$_2$—and its salts with a non-toxic, pharmaceutically acceptable acid or base.

2. A compound of claim 1 wherein Y is —(CH$_2$)$_n$—N—(CH$_2$)$_p$—, R$_{13}$ is hydrogen or alkyl of 1 to 6 carbon atoms and n and p are individually integers from 0 to 6.

3. A compound of claim 1 wherein A is selected from the group consisting of

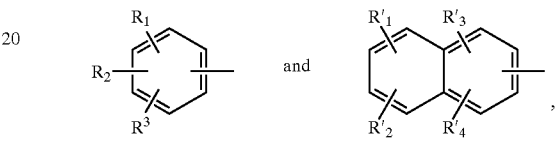

R$_1$, R$_2$ and R$_3$ are individually selected from the group consisting of hydrogen, —OH,

and alkyl and alkoxy of 1 to 6 carbon atoms or R$_1$ and R$_2$ or R$_2$ and R$_3$ together form methylenedioxy, R$_5$ and R$_6$ are individually selected from the group consisting of hydrogen and alkyl of 1 to 6 carbon atoms or R$_1$ and R$_2$ or R$_2$ and R$_3$ together form methylenedioxy, R$_5$ and R$_6$ are individually selected from the group consisting of hydrogen and alkyl of 1 to 6 carbon atoms, R'$_1$, R'$_2$ R'$_3$ and R'$_4$ are individually selected from the group consisting of hydrogen, —OH and alkoxy of 1 to 6 carbon atoms, R$_8$ is hydrogen, X is —NH—CO— or —CO—Q—, Q is piperazine unsubstituted or substituted with 1 or 2 methyl, Y is —(CH$_2$)$_n$—N—(CH$_2$)$_p$—, R$_{13}$ is hydrogen or alkyl of 1 to 6 carbon atoms, p and n are individually an integer of 0 to 6 or Y is alkyl, alkenyl and alkynyl of up to 10 carbon atoms and R$_{10}$ is hydrogen or methyl.

4. A compound of claim 1 wherein R$_5$ and R$_6$ are individually hydrogen or methyl or ethyl and at least one of R'$_1$, R'$_2$, R'$_3$ and R'$_4$ is —OH.

5. A compound of the formula

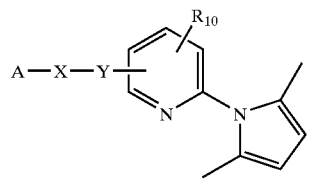

wherein A is selected from the group consisting of

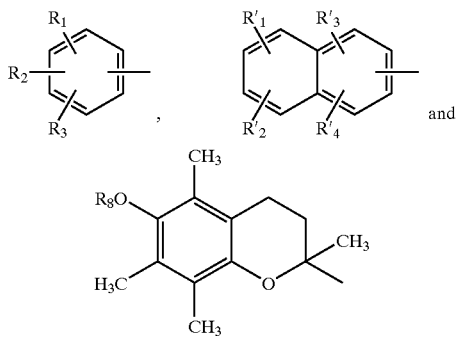

$R_1$, $R_2$ and $R_3$ are individually selected from the group of hydrogen, halogen, —OH, —SK, alkyl and alkoxy of 1 to 6 carbon atoms, aralkyl of 1 to 6 alkyl carbon atoms, —O—CO—$R_4$, —$SR_4$,
—S(O)$R_4$, —$SO_2R_4$ and

or
$R_1$, and $R_2$ or $R_2$ and $R_3$ together form methylenedioxy, $R_4$ is alkyl of 1 to 6 carbon atoms, $R_5$ and $R_6$ are individually selected from the group consisting of hydrogen, alkyl of 1 to 6 carbon atoms and aryl unsubstituted or substituted with at leas one remember of the group consisting of halogen, —OH and alkyl and alkoxy of 1 to 6 carbon atoms or taken with the nitrogen form a heterocycle of 4 to 6 ring member containing 1 to 2 members of the group consisting of —O—, —S— and —$NR_7$—, $R_7$ is hydrogen or alkyl of 1 to 6 carbon atoms, $R'_1$, $R'_2$, $R'_3$, $R_4$ are individually selected from the group consisting of hydrogen, halogen, —OH and alkoxy of 1 to 6 carbon atoms, X is selected from the group consisting of
alkenyl of up to 6 carbon atoms, Q is selected from the group consisting of (1) piperazine, homopiperazine, piperidine, pyrrolidine and azetidine, each unsubstituted or substitute with least one alkyl of 1 to 6 carbon atoms and (2) a single bond, W is selected from the group consisting of =O, =S and =NH, Z is phenylene or phenylene substituted with at least one halogen, m is an integer from 0 to 6, Y is selected from the group consisting of (1) alkyl alkenyl and alkynyl of up to 10 carbon atoms, each
unsubstituted or unsubstituted with

and (2) —$(CH_2)_m$—O—$(CH_2)_p$——$CH_{2n}$—S—$(CH_2)_p$— and —$(CH_2)_n$—$NR_{13}$—$(CH_2)_p$—, n and p are individually integers from 0 to 6, $R_{10}$ is selected from the group consisting of hydrogen, —OH, —CN, $NO_2$, —$SR_{15}$ and alkyl and alkoxy of 1 to 6 carbon atoms, $R^{11}$, $R_{12}$, $R_{13}$, $R_{14}$ and $R_{15}$ are individually hydrogen or ally of 1 to 6 carbon atoms, $R_{11}$ is selected from the group consisting of hydrogen and alkyl and thioalkyl of 1 to 6 carbon atoms and Y is alkylene of 1 to 8 carbon atoms, with the provisos (1) that —X—Y— together cannot be a member selected from the group consisting of a single bond, alkylene, —O—, —S—, —NH— and —NH—CO—NH—alkylene, (2) that when A is phenyl, —X—Y— is not —NH—CO—NH— and (3) when A in formula III is phenyl or naphthyl or phenyl substituted with at least one halogen, X is not —NH—CO— or —CO—Q and Q is pip line.

6. A compound of claim 1 selected from the group consisting of:
6-amino-N-[3,5-bis-(1,1-dimethylethyl)-4-hydroxyphenyl]-4-methyl-2-pyridine-pentanamide hydrochloride;
6-amino-N-[3,5-bis-(1,1-dimethylethyl)-4-hydroxyphenyl]-4-methyl-2-pyridine-butanamide hydrochloride;
6-amino-N-[4-dimethylamino)phenyl]-4-methyl-2-pyridinebutanamide hydrochloride;
N-[(6-amino-4-methyl-2-pyrdinyl)butyl]-2-hydroxy-5-methoxybenzamide hydrochloride;
N-[(6-amino-4-methyl-2-pyrdinyl)butyl]-2,6-dihydroxybenzamide;
N-[(6-amino-4-methyl-2-pyrdinyl)butyl]-2,5-dihydroxybenzamide hydrochloride;
5-amino-N-[(6-amino-4-methyl-2-pyrdinyl)butyl]-2-hydroxybenzamide hydrochloride;
N-[(6-amino-4-methyl-2-pyrdinyl)butyl]-2,5-dihydroxy-3-methylbenzamide hydrochloride;
N-[(6-amino-4-methyl-2-pyrdinyl)butyl]-2,5-dihydroxy-3-(1-methylethyl)-benzamide;
N-[(6-amino-4-methyl-2-pyrdinyl)butyl]-2-hydroxy-4,6-dimethoxy-benzamide hydrochloride;
N-[(6-amino-4-methyl-2-pyrdinyl)butyl]-3,5-bis-(1,1-dimethylethyl)-4-hydroxy-benzamide hydrochloride;
6-amino-N-[3,5-bis(1,1-dimethylethyl)-4-hydroxyphenyl]-4-methyl-2-pyridineheptanamide hydrochloride;
6-amino-N-[3,5-bis(1,1-dimethylethyl)-4-hydroxyphenyl]-4-methyl-2-pyridineheptanamide hydrochloride;
6-amino-N-[3,5-bis(1,1-dimethylethyl)-4-hydroxyphenyl]-4-methyl-2-pyridineheptanamide hydrochloride;
α-amino-N-[4-(dimethylamino)phenyl]-5-(6-amino-2-pyridinyl)-4-pentynamide hydrochloride;
α-diamino-N-[4-(dimethylamino)phenyl]-2-pyridinylpentanamide hydrochloride;
6-amino-N-[4-(dimethylamino)phenyl]-4-methyl-2-pyridinehexanamide hydrochloride;
6-amino-N-[4-(diemthylamino)phenyl]-4-methyl-2-pyridinehexanamide hydrochloride;
N-[(6-amino-4-methyl-2-pyridinyl)butyl]-1,3-benzodioxole-5-carboxamide hydrochoride;
6-amino-N-[(diemthylamino)phenyl]-4-methyl-2-pyridinehexanamide hydrochloride;
{[4-(6-amino-4-methyl-2-pyridinyl)butyl]amino}-N-[(4-dimethylamino)phenyl]-acetamide hydrochloride;
6-amino-N-[3-(4-hydroxy-3-methoxy-phenyl)-2-propenyl]-4-methyl-2-pyridine-butanamine hydrochloride;
6-amino-N-[4-chloro-2-(phenylamino)phenyl]-4-methyl-2-pyridinepentanamide hydrochloride;

N-[(6-amino-4-methyl-2-pyridinyl)butyl]-1,3-benzodioxole-5-acetamide hydrochloride;

N-[4-(6-amino-4-methyl-2-pyridinyl)butyl]-N-(1,3-benzodioxole-5-ylmethyl)amine fumarate;

N-[4-(6-amino-4-methyl-2-pyridinyl)butyl]-N-[(E)-3-2-propenyl]amine fumarate;

(E)-N-[(6-amino-4-methyl-2-pyridinyl)butyl]-3-(1,3-benzodioxol-5-yl)-2-propenamide fumarate;

2-({[4-(6-amino-4-methyl-2-pyridinyl)butyl]amino}methyl)-4-methoxphenol;

N-[2-(benzyloxy)-4,5-dimethoxybenzyl]-4-[6-(2,5-dimethyl-1H-pyrrol-1-yl)-4-methyl-2-pyridinyl]-1-butanamine;

-6-(4-{[2-(benzyloxy)-4,5-dimethoxybenzyl]amino}butyl)-4-methyl-2-pyridinamine;

2-({[4-(6-amino-4-methyl-2-pyridinyl)butyl]amino}methyl)-4,5-dimethoxyphenol.

7. A compound of claim 6, characterized in that it is one of the following compounds:

6-amino-N-[3,5-bis-(1,1-dimethylethyl)-4-hydroxyphenyl]-4-methyl-2-pyridinepentanamide hydrochloride;

6-amino-N-[4-(dimethylamino)phenyl]-4-methyl-2-pyridinebutanamide hydrochloride;

1-[2-(6-amino-4-methyl-2-pyridinyl)ethyl]-4-[(3,4-dihydro-6-hydroxy-2,5,7,8-tetramethyl-2H-[1]-benzopyran-2-yl)carbonyl]-piperazine hydrochloride;

N-[(6-amino-4-methyl-2-pyridinyl)butyl]-2-hydroxy-5-methoxy-benzamide hydrochloride;

N-[(6-amino-4-methyl-2-pyridinyl)butyl]-2,5-dihydroxy-benzamide hydrochloride;

N-[(6-amino-4-methyl-2-pyridinyl)butyl]-2,5-dihydroxy-3-methyl-benzamide hydrochloride;

N-[(6-amino-4-methyl-2-pyridinyl)butyl]-2,5-dihydroxy-3-(1-methylethyl)-benzamide;

6-amino-N-[4-(dimethylamino)phenyl]-4-methyl-2-pyridinehexanainide hydrochloride;

N-[(6-amino-4-methyl-2-pyridinyl)butyl]-1,3-benzodioxole-5-carboxamide hydrochloride;

6-amino-N-[4-(dimethylamino)phenyl]-4-methyl-2-pyridinepentananamide hydrochloride;

{[4-(6-amino-4-methyl-2-pyridinyl)butyl]amino}-N-[(4-dimethylamino)phenyl]acetamide hydrochloride;

6-amino-N-[3-(4-hydroxy-3-methoxy-phenyl)-2-propenyl]-4-methyl-2-pyridinebutanamine hydrochloride.

8. A compound of claim 7, characterized in that it is one of the following compounds:

6-amino-N-[3,5-bis-(1,1-dimethylethyl)-4-hydroxyphenyl]-4-methyl-2-pyridinepentanamide hydrochloride;

N-[(6-amino-4-methyl-2-pyridinyl)butyl]-2,5-dihydroxy-3-(1-methylethyl)-benzamide;

6-amino-N-[4-(dimethylamino)phenyl]-4-methyl-2-pyridinepentananamide hydrochloride;

{[4-(6-amino-4-methyl-2-pyridinyl)butyl]amino}-N-[(4-dimethylamino)phenyl]-acetamide hydrochloride;

6-amino-N-[3-(4-hydroxy-3-methoxy-phenyl)-2-propenyl]-4-methyl-2-pyridine-butanamine hydrochloride;

2-({[4-(6-amino-4-methyl-2-pyridinyl)butyl]amino}methyl)-4,5-dimethoxyphenol.

9. A method of inhibiting lipidic peroxidation in a mammal in need thereof comprising administering to said mammal an effective amount of a compound of the formula

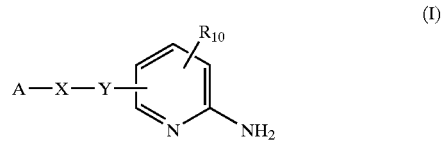

(I)

wherein A is selected from the group consisting of

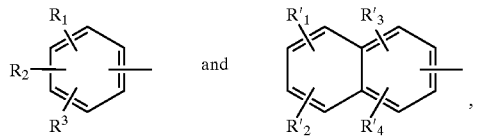

$R_1$, $R_2$ and $R_3$ are individually selected from the group consisting of hydrogen, halogen, —OH, —SH, alkyl and alkoxy of 1 to 6 carbon atoms, aralkoxy of 1 to 6 alkyl carbon atoms, —O—CO—$R_4$, S$R_4$, —S(O)—$R_4$, —SO$_2$-$R_4$ and

or $R_1$ and $R_2$ or $R_2$ and $R_3$ form methylenedioxy, $R_4$ is alkyl of 1 to 6 carbon atoms, $R_5$ and $R_6$ are individually selected from the group consisting of hydrogen, alkyl of 1 to 6 carbon atoms and aryl unsubstituted or substituted with at least one member of the group consisting of halogen, —OH and alkyl and alkoxy of 1 to 6 carbon atoms or taken together with the nitrogen form a heterocycle of 4 to 6 ring members containing 1 to 2 members of the group consisting of oxygen, sunfir and =N$R_7$, $R_7$ is drogen or alkyl of 1 to 6 carbon atoms, R'$_1$, R'$_2$, $R_3$ and R'$_4$ are individually selected from the group consisting of hydrogen, halogen, —OH and alkoxy of 1 to 6 carbon atoms, X is selected from the group consisting of

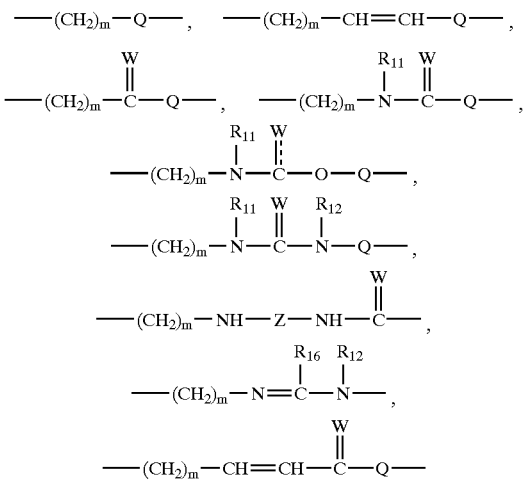

and alkenyl up to 6 carbon atoms, Q is selected from the group consisting of a single bond, piperazine, homopiperazine, piperidine, pyrrolidine and azetidine, each unsubstituted or substituted by at least one alkyl of 1 to 6 carbon atoms, W is selected from the group consisting of =O, =S and —NH, Z is phenylene or phenylene substituted by at least one halogen, m is an integer from 0 to 6, Y is selected from the group consisting of a) alkyl, alkenyl and alkynyl of up to 10 carbon atoms unsubstituted or substituted by

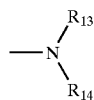

and b) —(CH$_2$)$_n$—O—(CH$_2$)$_p$—

—CH$_2$)$_n$—S—(CH$_2$)$_p$— and —(CH$_2$)$_n$—NR$_{13}$—(CH$_2$)$_p$—, R$_{10}$ is selected from the group consisting of hydrogen, —OH, —CN, —NO$_2$, —SR$_{15}$ and alkyl and alkoxy of 1 to 6 carbon atoms, R$_{11}$, R$_{12}$, R$_{13}$, R$_{14}$ and R$_{15}$ are individually hydrogen or alkyl of 1 to 6 carbon atoms, R16 is selected from the group consisting of hydrogen and alkyl and thioallkyl of 1 to 6 carbon atoms with the provisos (1) —X—Y— are not selected from the group consisting of a single bond, alkylene, —O—, —S—, —NH— and —NH—CO—NH-alkylene and (2) when A is phenyl, —X—Y— together are not —NH—CO—NH— with the exception of N-(2-amino-6-methyl-3-pyridylmethy)-3,4,5-trimethoxy-benzamide, N-(2-amino-3-pyridylmethyl)-3,4,5-trimethoxy-benzamide, and N-2-amino-6-methyl-3-pyridylmethyl)-3,4,5-triethoxy-benzamide or its salts with non-toxic, pharmaceutically acceptable acids or bases to inhibit peroxidation.

10. A method of effecting neurodegenerative diseases in a mammal in need thereof comprising administering to said mammal an effective amount of a compound of the formula (I')

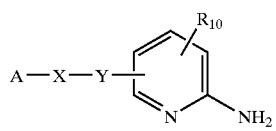

wherein A is selected from the group consisting of

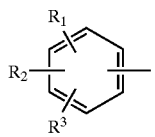 and 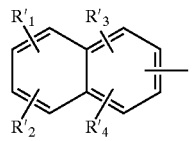

R$_1$, R$_2$ and R$_3$ are individually selected from the group consisting of hydrogen, halogen, —OH, —SH, and alkoxy of 1 to 6 carbon atoms, aralkoxy of 1 to 6 carbon atoms, —O—CO—R$_4$, —SR$_4$, —S(O)—R$_4$, —SO$_2$—R$_4$ and

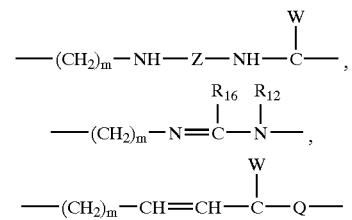

and alkenyl up to 6 carbon atoms, Q is selected from the group consisting of a single bond, piperazine, hormopiperazine, piperadine, pyrroline and azetidine, each unsubstituted or substituted by at least one alkyl of 1 to 6 carbon atoms, W is selected from the group consisting of =O, =S and =NH, Z is phenylene or phenylene substituted by at least one halogen, m is an integer from 0 to 6, Y is selected from the group consisting of a) alkyl, alkenyl and alkynyl of up to 10 carbon atoms,

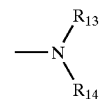

and b) CH$_2$)$_n$—O—(CH$_2$)$_p$—, —(CH$_2$)n-S—(CH$_2$)$_p$— and —CH$_n$NR$_{13}$—(CH$_2$)$_p$—, R$_{10}$ is selected from the group consisting of hydrogen, —OH, —CN, —NO$_2$, —SR$_{13}$ and alkyl and alkoxy of 1 to 6 carbon atoms, R$_{11}$, R$_{12}$, R$_{13}$, R$_{14}$ and R$_{15}$ are individually hydrogen or alkyl of 1 to 6 carbon atoms, R$_{16}$ is selected from the group consisting of hydrogen and alkyl and thioalkyl of 1 to 6 carbon atoms with the provisos (1) —X—Y are not selected from the group consisting of a single bond, alkylene, —O—, —S—, —NH— and —NH—CO—NH—alkylene and (2) when A is phenyl, —X—Y— together are not —NH—CO—NH— with the exception of N-(2-amino-6-methyl-3-pyridylmethyl)-3,4,5-trimethoxy-benzamide, N-(2-amino-3-pyridylmethyl)-3,4,5-trimethoxy-benzamide and N-2-amino-6-methyl-3-pyridylmethyl)-3,4,5-triethoxy-benzamide or its salts with non-toxic, pharmaceutically acceptable acids or bases to treat neurodegenerative diseases.

11. The method of claim 10 wherein the neurodegenerative disease is Parkinson's disease.

12. The method of claim 11 wherein the compound administered is 6-amino-N-[3,5-bis-(1,1-dimethylethyl)-4-hydroxyphenyl)-4-methyl-2-pyridinepentanamide or its salt with non-toxic, pharmaceutically acceptable acids or bases.

13. A method for relieving pain in a mammal in need thereof comprising administering to said mammal an effective amount of a compound of the formula (I)' as defined in claim 10, or its salts with non-toxic, pharmaceutically acceptable acids or bases, to relieve pain.

14. A method for treating cardio-vascular and cerebro-vascular disorders in a mammal in need thereof comprising administering to said mammal an effective amount of a compound of the formula (I)' as defined in claim 10, or its salts with non-toxic, pharmaceutically acceptable acids or bases, to treating cardiovascular and cerebro-vascular disorders.

15. The method of claim 14 wherein the cardio-vascular and cerebro-vascular disorders are ischemic or hemorragic cardiac or cerebral infarctions.

* * * * *